US010011587B2

(12) United States Patent
Li et al.

(10) Patent No.: US 10,011,587 B2
(45) Date of Patent: Jul. 3, 2018

(54) MULTIVALENT LIGANDS TARGETING VEGFR

(71) Applicant: THE METHODIST HOSPITAL SYSTEM, Houston, TX (US)

(72) Inventors: Zheng Li, Houston, TX (US); Feng Li, Sugar Land, TX (US)

(73) Assignee: The Methodist Hospital System, Houston, TX (US)

( * ) Notice: Subject to any disclaimer, the term of this patent is extended or adjusted under 35 U.S.C. 154(b) by 0 days.

(21) Appl. No.: 15/311,323

(22) PCT Filed: May 14, 2015

(86) PCT No.: PCT/US2015/030715
§ 371 (c)(1),
(2) Date: Nov. 15, 2016

(87) PCT Pub. No.: WO2015/175750
PCT Pub. Date: Nov. 19, 2015

(65) Prior Publication Data
US 2017/0073328 A1 Mar. 16, 2017

Related U.S. Application Data

(60) Provisional application No. 61/993,682, filed on May 15, 2014.

(51) Int. Cl.
C07D 401/14 (2006.01)
C07D 239/94 (2006.01)
C07D 403/12 (2006.01)
C07D 403/14 (2006.01)
A61K 49/00 (2006.01)
A61K 51/04 (2006.01)
C07D 405/14 (2006.01)

(52) U.S. Cl.
CPC ........ C07D 401/14 (2013.01); A61K 49/0043 (2013.01); A61K 49/0052 (2013.01); A61K 51/0482 (2013.01); C07D 239/94 (2013.01); C07D 403/12 (2013.01); C07D 403/14 (2013.01); C07D 405/14 (2013.01); C07B 2200/05 (2013.01)

(58) Field of Classification Search
CPC .................................................. C07D 401/14
See application file for complete search history.

(56) References Cited

U.S. PATENT DOCUMENTS

RE42,353 E     5/2011   Thomas et al.
2004/0229293 A1  11/2004  Chan-Hui et al.
2008/0254497 A1  10/2008  Singh et al.

FOREIGN PATENT DOCUMENTS

CN       103483276 A    1/2014

OTHER PUBLICATIONS

Kim et al., Specific Binding of Modified ZD6474 (Vandetanib) Monomer and Its Dimer with VEGF Receptor 2 Bioconjugate Chemistry (2013), 24(11), 1937-1944.*
International Preliminary Report on Patentability issued in International Application No. PCT/US15/30715, dated Nov. 24, 2016.
International Search Report and Written Opinion issued in International Application No. PCT/US2015/0030715, dated Sep. 29, 2015.
Kim, et al., "Specific Binding of Modified ZD6474 (Vandetanib) Monomer and Its Dimer with VEGF Receptor-2", Bioconjugate Chem. 2013; 24:1937-1944 (abstract).
Li, et al., "A Tyrosine Kinase Inhibitor-Based High-Affinity PET Radiopharmaceutical Targets Vascular Endothelial Growth Factor Receptor", J. Nuclear Med. 2014, 1525-1531.
Awasthi, et al., "Endothelial monocyte activating polypeptide II interferes with VEGF-induced proangiogenic signaling", Laboratory Investigation. 2009; 89(1):38-46.
Backer, et al., "Imaging key biomarkers of tumor angiogenesis", Theranostics. 2012; 2(5):502-515.
Baluk P, et al., "Cellular abnormalities of blood vessels as targets in cancer", Current Opinion in Genetics & Development. 2005; 15(1):102-111.
Bergers G, et al., "Modes of resistance to anti-angiogenic therapy," Nat. Rev. Cancer. 2008; 8(8):592-603.
Cai, et al., "PET of vascular endothelial growth factor receptor expression", J. Nucl. Med. 2006; 47(12):2048-2056.
Chau Ng, et al., "Vandetanib for the treatment of medullary thyroid cancer", Clin. Cancer Res. 2013; 19:524-529.
Chen K, et al., "Quantitative PET imaging of VEGF receptor expression", Mol. Imaging Biol. 2009; 11(1):15-22.
Tai-Ping et al.,"Controlling vasculature: angiogenesis, anti-angiogenesis and vascular targeting of gene therapy", TiPS 1995; 16:57-66.
Ferrara N, et al., "The biology of VEGF and its receptors", Nature Med. 2003;9(6):669-676.
Ferrara N, et al., "Discovery and development of bevacizumab, an anti-VEGF antibody for treating cancer", Nature Rev. Drug Discovery. 2004; 3(5):391-400.
Flanigan J, et al., "Current status of vandetanib (ZD6474) in the treatment of non-small cell lung cancer", Biologics. 2010; 4:237-243.
Foersch S, et al., "Molecular imaging of VEGF in gastrointestinal cancer in vivo using confocal laser endomicroscopy", Gut. 2010; 59(8):1046-1055.
Folkman J. "Angiogenesis: an organizing principle for drug discovery?" Nature Rev. 2007; 6(4):273-286.

(Continued)

Primary Examiner — Paul V Ward
(74) Attorney, Agent, or Firm — Meunier Carlin & Curfman LLC

(57) ABSTRACT

Compounds that target vascular endothelial growth factor receptors for therapy and imaging are disclosed. Methods for making the compounds and detecting or imaging cells expressing VEGFR using the compounds are also provided. In accordance with the purposes of the disclosed subject matter, as embodied and broadly described herein, disclosed are compounds, and methods of making and using the compounds. The disclosed compounds, in one aspect, are quinazoline compounds.

16 Claims, 14 Drawing Sheets

(56) References Cited

OTHER PUBLICATIONS

Folkman J. "Angiogenesis in cancer, vascular, rheumatoid and other disease", Nature Med. 1995; 1:27-31.

Hao G, et al., "Peptoid-based PET imaging of vascular endothelial growth factor receptor (VEGFR) expression" Am. J. Nucl. Med. Mol. Imaging. 2001; 1(1):65-75.

Hennequin, et al., "Design and Structure-Activity Relationship of a New Class of Potent VEGF Receptor Tyrosine Kinase Inhibitors", J. Med. Chem. 1999;42:5369-5389.

Hicks J, et al., "Radiolabeled small molecule protein kinase inhibitors for imaging with PET or SPECT", Molecules. 2010; 15(11):8260-8278.

Jayson GC, et al., "Molecular imaging and biological evaluation of HuMV833 anti-VEGF antibody: implications for trial design of antiangiogenic antibodies", J. National Cancer Institute. 2002; 94(19):1484-1493.

Kang CM, et al., "In vivo characterization of (68)Ga-NOTA-VEGF (121) for the imaging of VEGF receptor expression in U87MG tumor xenograft models", European J. Nuclear Med. Mol. Imaging. 2013; 40(2):198-206.

Keana, "Newer Aspects of Synthesis and Chemistry of Nitroxide Spin Labels", Chemical Reviews, 1978; 78(1):37-64.

Kniess T. "Radiolabeled small molecule inhibitors of VEGFR—recent advances", Current Pharm. Design. 2012; 18(20):2867-2874.

Kuchar M, et al., "Radioiodinated sunitinib as a potential radiotracer for imaging angiogenesis-radiosynthesis and first radiopharmacological evaluation of 5-[125I]Iodo-sunitinib", Bioorg. & Med. Chem. Lett. 2012; 22(8):2850-2855.

Li F, et al., "Synthesis and evaluation of bivalent, peptidomimetic antagonists of the alphavbeta3 integrins", Bioorg. & Med. Chem. Lett. 2010;20(22):6577-6580.

Li F, et al., "Synthesis and evaluation of a near-infrared fluorescent nonpeptidic bivalent integrin alpha(v)beta(3) antagonist for cancer imaging", Bioconjugate Chem. 2010; 21(2):270-278.

Mammen M. "Polyvalent interactions in biological systems: Implications for design and use of multivalent ligands and inhibitors", Angewandte Chemie-International Edition. 1998; 37(20):2755-2794.

Meng Q, et al., "Novel 64Cu-labeled CUDC-101 for in vivo PET imaging of histone deacetylases", ACS Med. Chem. Lett. 2013; 4:858-862.

Michalski MH, et al., "Molecular imaging in cancer treatment", European J. Nucl. Med. Mol. Imaging. 2011; 38(2):358-377.

Nagengast WB, et al., "89Zr-bevacizumab PET of early antiangiogenic tumor response to treatment with HSP90 inhibitor NVP-AUY922", J. Nucl. Med. 2010; 51(5):761-767.

Olsson Ak, et al., "VEGF receptor signaling—in control of vascular function", Nature Rev. Mol. Cell Biol. 2006; 7(5):359-371.

Paez-Ribes M, et al. "Antiangiogenic therapy elicits malignant progression of tumors to increased local invasion and distant metastasis", Cancer Cell. 2009; 15(3):220-231.

Prabhakaran J, et al., "Synthesis and in vitro evaluation of [18F](R)-FEPAQ: a potential PET ligand for VEGFR2", Bioorg. & Med. Chem. Lett. 2012; 22(15):5104-5107.

Rodriguez-Porcel M, et al., "Imaging of VEGF receptor in a rat myocardial infarction model using PET", J. Nucl. Med. 2008; 49(4):667-673.

Roskoski R., "Vascular endothelial growth factor (VEGF) signaling in tumor progression", Critical Rev. Oncology Hematology. 2007; 62(3):179-213.

Samén E, et al., "Synthesis and preclinical evaluation of [11C]PAQ as a PET imaging tracer for VEGFR-2", European J. Nucl. Med. Mol. Imaging. 2009; 36:1283-1295.

Scheer MG, et al. "Imaging liver metastases of colorectal cancer patients with radiolabelled bevacizumab: Lack of correlation with VEGF-A expression", European J. Cancer. 2008; 44(13):1835-1840.

Schenone S, et al., "Antiangiogenic agents: an update on small molecule VEGFR inhibitors", Current Med. Chem. 2007; 14(23):2495-2516.

Simons M. "Angiogenesis—Where do we stand now?" Circulation. 2005; 111(12):1556-1566.

Takahashi Y, et al., "Expression of Vascular Endothelial Growth-Factor and Its Receptor, Kdr, Correlates with Vascularity, Metastasis, and Proliferation of Human Colon-Cancer", Cancer Research. 1995; 55(18):3964-3968.

Tolmachev V, et al., "Radiolabelled receptor-tyrosine-kinase targeting drugs for patient stratification and monitoring of therapy response: prospects and pitfalls", The Lancet Oncology. 2010;11(10):992-1000.

Underiner TL, et al., "Development of vascular endothelial growth factor receptor (VEGFR) kinase inhibitors as anti-angiogenic agents in cancer therapy". Current Med. Chem. 2004; 11(6):731-745.

Van Der Bilt, et al., "Measurement of Tumor VEGF-A Levels with Zr-89-Bevacizumab PET as an Early Biomarker for the Antiangiogenic Effect of Everolimus Treatment in an Ovarian Cancer Xenograft Model", Clinical Cancer Research. 2012; 18(22):6306-6314.

Waerzeggers Y, et al., "Specific biomarkers of receptors, pathways of inhibition and targeted therapies: pre-clinical developments", British J. Radiology. 2011; 84 Spec No 2:S168-178.

Wang H, et al., "A new PET tracer specific for vascular endothelial growth factor receptor 2", European J. Nucl. Med. Mol. Imaging. 2007; 34(12):2001-2010.

Wang H, et al., "Site-Specific Labeling of scVEGF with Fluorine-18 for Positron Emission Tomography Imaging", Theranostics 2012; 2(6):607-617.

Zhang J, et al., "Molecular imaging of vascular endothelial growth factor receptors in graft arteriosclerosis", Arteriosclerosis, Thrombosis, Vascular Biol. 2012; 32(8):1849-1855.

Zhang Y, et al., "Positron Emission Tomography Imaging of Vascular Endothelial Growth Factor Receptor Expression with (61)Cu-Labeled Lysine-Tagged VEGF(121)", Mol. Pharm. 2012; 9(12):3586-3594.

* cited by examiner

MULTIVALENT LIGANDS TARGETING VEGFR

CROSS REFERENCE TO RELATED APPLICATIONS

This application claims the benefit of priority to U.S. Provisional Application 61/993,682 filed May 15, 2014, the disclosure of which is incorporated by reference herein in their entireties.

FIELD

The disclosed subject matter relates generally to compounds for angiogenesis targeted therapy and imaging, in particular deleterious angiogenesis associated with diseases such as cancer.

BACKGROUND

Normal angiogenesis plays an important role in a variety of processes including embryonic development, wound healing and several components of female reproductive function. Deleterious angiogenesis has been associated with disease states including diabetic retinopathy, psoriasis, cancer, rheumatoid arthritis, atheroma, Kaposi's sarcoma and haemangioma (Fan et al., 1995, *Trends Pharmacol. Sci.* 16:57-66; Folknan, 1995, *Nature Medicine* 1:27-31). Vascular endothelial growth factors (VEGFs) are regulators of angiogenesis. VEGF binds to tyrosine kinase receptors on the cell surface, known as VEGFR1 (Flt-1), VEGFR2 (Flk-1, KDR), and VEGFR3 (Flt-4). This results in stimulation of the receptor-associated tyrosine kinase activity, which leads to phosphorylation of tyrosine residues on both the receptor and other intracellular molecules. These changes in tyrosine phosphorylation initiate a signaling cascade leading to a variety of cellular responses including inducing endothelial cell proliferation, promoting cell migration, and inhibiting apoptosis.

U.S. Pat. No. RE42,353 discloses certain quinazoline compounds that inhibit the effects of VEGF. The quinazoline compounds are useful for treating diseases associated with angiogenesis and/or increased vascular permeability such as cancer, diabetes, psoriasis, rheumatoid arthritis, Kaposi's sarcoma, haemangioma, acute and chronic nephropathies, atheroma, arterial restenosis, autoimmune diseases, acute inflammation, and ocular diseases with retinal vessel proliferation. However, a wide variability in response to treatment with these drugs has been observed in cancer patients.

Michalski et al. developed radio-labeled VEGF/VEGFR antibodies for imaging VEGFR expression in various disease models (*European J Nuclear Med Mol Imaging*, 2011, 38:358-377). However, these probes exhibit low to moderate tumor-to-background ratio in VEGFR expressing cells, despite their high receptor affinity. The imaging potential of these probes are also limited by the slow clearance of antibodies from the blood, high uptake in non-targeted tissues such as kidney, and poor extravasations and diffusion into the extracellular space.

What are needed are compounds and methods to non-invasively determine VEGFR expression levels in cells in vivo. Further, compounds that bind selectively to VEGFR expressing cells are also needed. Still further, what are needed are compounds that exhibit fast clearance from the blood and/or exhibit low uptake in non-targeted tissues such as the kidney. The compositions and methods disclosed herein address these and other needs.

SUMMARY

In accordance with the purposes of the disclosed subject matter, as embodied and broadly described herein, disclosed are compounds, and methods of making and using the compounds. The disclosed compounds, in one aspect, are quinazoline compounds. The quinazoline compounds can target vascular endothelial growth factor receptors (VEGFR) for therapy and imaging of VEGFR expression. In a specific aspect, compounds of Formula I, Formula IV, and Formula VIII are disclosed:

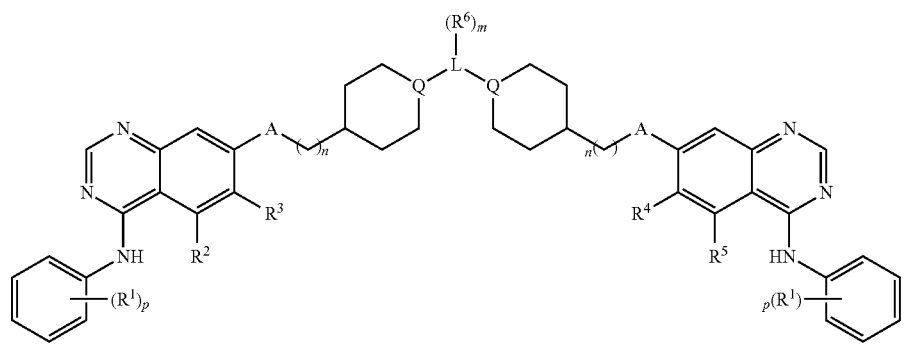

Formula I

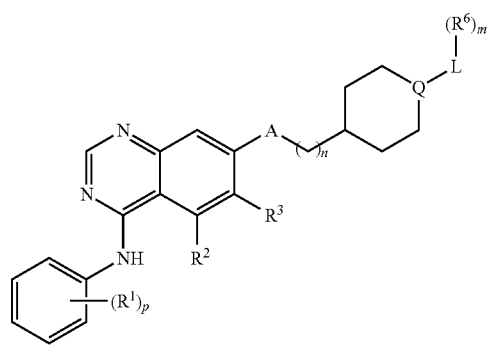

Formula IV

-continued

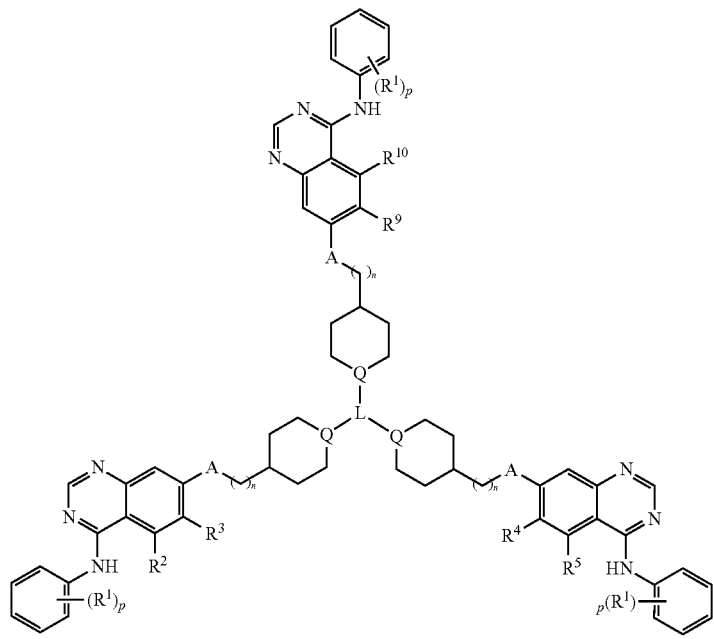

Formula VIII wherein,

R$^1$ can be hydroxyl, halogen, C$_{1-3}$ alkyl, C$_{1-3}$ alkoxyl, C$_{1-3}$ alkanoyloxyl, trifluoromethyl, cyano, amino, or nitro;

R$^2$, R$^3$, R$^4$, R$^5$, R$^9$, and R$^{16}$ can be, independently of one another, hydrogen, hydroxyl, halogen, nitro, trifluoromethyl, cyano, C$_{1-3}$ alkyl, C$_{1-3}$ alkoxyl, C$_{1-3}$ alkylthio, or —NR$^7$R$^8$, wherein R$^7$ and R$^8$, which can be the same or different, each represents hydrogen or C$_{1-3}$ alkyl;

A can be oxygen, —CH$_2$—, —S—, —SO—, —SO$_2$—, —NR$^7$CO—, —CONR$^7$—, —SO$_2$NR$^7$—, —NR$^7$SO$_2$—, or NR$^7$—;

Q can be nitrogen, or —CH—;

L is a linker;

R$^6$ is a detectable moiety a therapeutic moiety or both;

n is an integer from 1 to 5;

m is an integer from 1 to 5; and p is an integer from 1 to 4.

The detectable moiety can be a near-infrared label, a fluorescent label, a radiolabel, a magnetic spin resonance label, a chromophore, a VEGFR ligand, or any combination thereof. The therapeutic moiety can be radioisotopes for radiation therapy such as Y-90 or Lu-177 etc or a chemotherapy drug. The linker L can be an alkyl, alkenyl, amine, amide, alkylamine, thioether, sulfonyl, sulfinyl, cycloalkyl, carboxylate, aryl, heterocycloalkyl, heteroaryl, or cycloalkenyl.

Methods for making the disclosed compounds and detecting or imaging cells expressing VEGFR using these compounds are also disclosed. The cells expressing VEGFR can be cancer cells, hyperproliferative cells, or any combination thereof.

Additional advantages will be set forth in part in the description which follows, and in part will be obvious from the description, or may be learned by practice of the subject matter disclosed herein. It is to be understood that both the foregoing general description and the following detailed description are exemplary and explanatory only and are not restrictive of the invention, as claimed.

BRIEF DESCRIPTION OF THE FIGURES

The accompanying figures, which are incorporated in and constitute a part of this specification, illustrate several embodiments of the invention and together with the description, serve to explain the principles of the disclosed subject matter.

FIG. 6B is a graph showing a comparison of tumor to muscle uptake ratios after injection of $^{64}$Cu-DOTA-ZD-G1, $^{64}$Cu-DOTA-ZD-G2 and $^{64}$Cu-DOTA-ZD-G2 with co-injection of 60 μg of ZD-G2. Data shown represent mean±SD (n≥3 per group).

FIG. 9A shows the fluorescence intensity of 6-FAM-conjugated ZD6474-monomer and ZD6474-dimer uptake by MDA-MB-231 cells. FIG. 9B shows quantification of FIG. 9A. FIG. 9C shows an intensity comparison of 6-FAM conjugated ZD6474-dimer uptake by MDA-MB-231 cell and HUVEC cell. FIG. 9D shows quantification of FIG. 9C at 3 h. FIG. 9E shows comparative expression of VEGFR-2 in three cell lines.

FIG. 10A shows blocking of ZD6474-dimer-FAM with 100× ZD6474-dimer. FIGS. 10B-10C shows a comparison of blocking efficiency between ZD6474-monomer and ZD6474-dimer.

FIG. 14A shows the raw photon counts and FIG. 14B shows the radiant efficiency (photon counts per unit time per unit area normalized by incident photon flux). Tumor and kidney values are averaged within the same animal FIG. 14C shows a close-up of tumor uptake and FIG. 14D shows the estimated total tumor accumulation as a percent of the injected dose. The difference between monomer and dimer uptake is highly significant (P<0.001).

DETAILED DESCRIPTION

Figure 1:
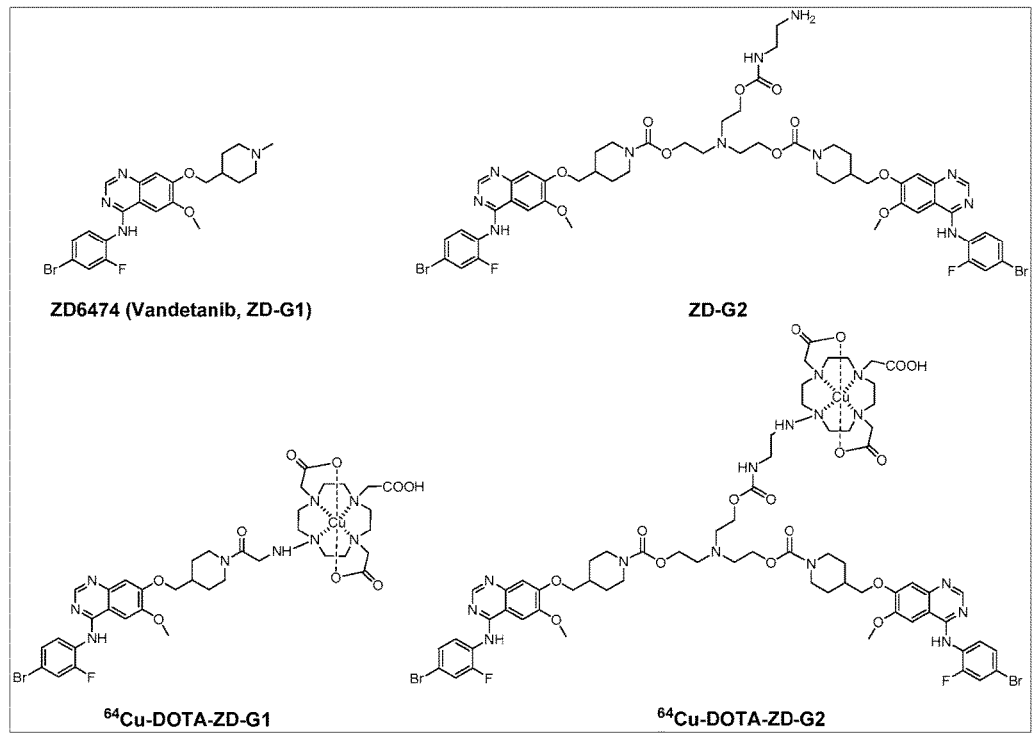
FIG. 1 shows the chemical structures of ZD6474 (ZD-G1), ZD-G2, $^{64}$Cu-DOTA-ZD-G1, $^{64}$Cu-DOTA-ZD-G2, and ZD-G3.
Figure 1:
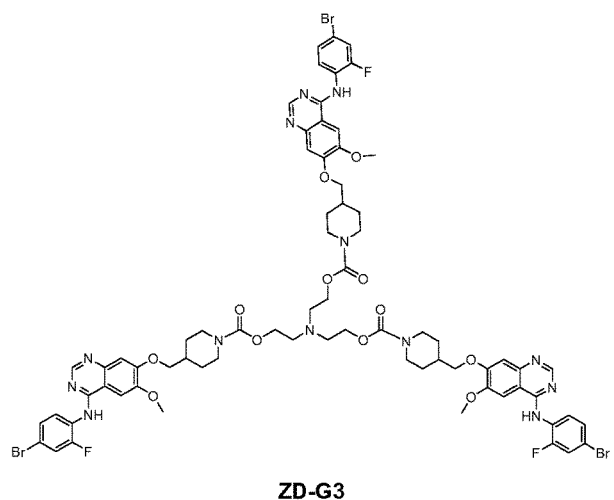

The disclosed subject matter can be understood more readily by reference to the following detailed description and the Examples included herein and to the Figures and their previous and following description.

Definitions

Before the present compounds, compositions, and methods are disclosed and described, it is to be understood that this invention is not limited to specific synthetic methods, or specific route of administration, as such may, of course, vary. It is also to be understood that the terminology used herein is for the purpose of describing particular embodiments only and is not intended to be limiting.

Throughout this application, various publications are referenced. The disclosures of these publications in their entireties are hereby incorporated by reference into this application in order to more fully describe the state of the art to which this invention pertains.

As used in the specification and the appended claims, the singular forms "a," "an," and "the" include plural referents unless the context clearly dictates otherwise. Thus, for example, reference to "a compound" includes mixtures of such compounds and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. Unless stated to the contrary, the term "about" means within 5%, e.g., within 1, 2, 3, or 4% of the stated value, or less.

In this specification and in the claims which follow, reference will be made to a number of terms which shall be defined to have the following meanings:

"Optional" or "optionally" means that the subsequently described event or circumstance does or does not occur, and that the description includes instances where said event or circumstance occurs and instances where it does not. For example, the phrase "optionally substituted alkyl" means that the alkyl group is or is not substituted and that the description includes both unsubstituted lower alkyl and lower alkyl where there is substitution.

An "effective amount", e.g., of the compounds or compositions described herein, refers to an amount of the compound in a composition or formulation which, when administered as part of a desired dosage regimen, brings about a change, e.g., in the rate of cell proliferation and/or the state of differentiation of a cell and/or rate of survival of a cell according to clinically acceptable standards for the disorder to be treated or, e.g., is taken up in a sufficient amount by VEGFR expressing cells such that the cells can be imaged by confocal microscopic imaging, CT imaging, PET imaging, MRI, or any combination thereof according to clinically acceptable standards for imaging cells.

"Pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio. Pharmaceutically acceptable materials are known to those of ordinary skill in the art.

"Half maximal inhibitory concentration" or "IC$_{50}$", as used herein, refers to a measure of the effectiveness of a compound in inhibiting biological or biochemical function. This quantitative measure indicates how much of a particular drug or other substance (inhibitor) is needed to inhibit a given biological process (or component of a process, i.e. an enzyme, cell, cell receptor or microorganism) by half. According to the FDA, $IC_{50}$ represents the concentration of a drug that is required for 50% inhibition in vitro. The $IC_{50}$ can be determined using a variety of assays known in the art.

"Analog" and "Derivative" are used herein interchangeably and refer to a compound that possesses the same core as the parent compound, but differs from the parent compound in bond order, the absence or presence of one or more atoms and/or groups of atoms, and combinations thereof. The derivative can differ from the parent compound, for example, in one or more substituents present on the core, which can include one or more atoms, functional groups, or substructures. In general, a derivative can be imagined to be formed, at least theoretically, from the parent compound via chemical and/or physical processes.

"Aliphatic", as used herein, refers to saturated or unsaturated groups containing carbon and hydrogen, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain aliphatic group has 30 or fewer carbon atoms in its backbone (e.g., $C_1$-$C_{30}$ for straight chain, $C_3$-$C_{30}$ for branched chain), more preferably 20 or fewer carbon atoms, more preferably 12 or fewer carbon atoms, and most preferably 8 or fewer carbon atoms. In some embodiments, the chain has 1-6 carbons. Likewise, preferred cycloalkyls have from 3-10 carbon atoms in their ring structure, and more preferably have 5, 6, or 7 carbons in the ring structure. The ranges provided above are inclusive of all values between the minimum value and the maximum value.

The term "alkyl" includes both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls.

The alkyl groups can also contain one or more heteroatoms within the carbon backbone. Examples include oxygen, nitrogen, sulfur, and combinations thereof. In certain embodiments, the alkyl group contains from one to four heteroatoms.

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "alkylthio" refers to an alkyl group, as defined above, having a sulfur radical attached thereto. In preferred embodiments, the "alkylthio" moiety is represented by one of —S— alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups. Alkylthio groups can be substituted as defined above for alkyl groups.

"Alkenyl" and "Alkynyl", as used herein, refer to unsaturated aliphatic groups containing one or more double or triple bonds analogous in length (e.g., $C_2$-$C_{30}$) and possible substitution to the alkyl groups described above.

"Aryl", as used herein, refers to 5-, 6- and 7-membered aromatic rings. The ring can be a carbocyclic, heterocyclic, fused carbocyclic, fused heterocyclic, bicarbocyclic, or biheterocyclic ring system, optionally substituted as described above for alkyl. Broadly defined, "Ar", as used herein, includes 5-, 6- and 7-membered single-ring aromatic groups that can include from zero to four heteroatoms. Examples include, but are not limited to, benzene, pyrrole, furan, thiophene, imidazole, oxazole, thiazole, triazole, pyrazole, pyridine, pyrazine, pyridazine and pyrimidine. Those aryl groups having heteroatoms in the ring structure can also be referred to as "heteroaryl", "aryl heterocycles", or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, and —CN. The term "Ar" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles, or both rings are aromatic.

"Alkylaryl", as used herein, refers to an alkyl group substituted with an aryl group (e.g., an aromatic or hetero aromatic group).

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, containing carbon and one to four heteroatoms each selected from non-peroxide oxygen, sulfur, and N(Y) wherein Y is absent or is H, O, ($C_{1-4}$) alkyl, phenyl or benzyl, and optionally containing one or more double or triple bonds, and optionally substituted with one or more substituents. The term "heterocycle" also encompasses substituted and unsubstituted heteroaryl rings. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heteroaryl", as used herein, refers to a monocyclic aromatic ring containing five or six ring atoms containing carbon and 1, 2, 3, or 4 heteroatoms each selected from non-peroxide oxygen, sulfur, and N(Y) where Y is absent or is H, O, ($C_1$-$C_8$) alkyl, phenyl or benzyl. Non-limiting examples of heteroaryl groups include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide) and the like. The term "heteroaryl" can include radicals of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl include, but are not limited to, furyl, imidazolyl, triazolyl, triazinyl, oxazoyl, isoxazoyl, thiazolyl, isothiazoyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. Aroxy can be represented by —O-aryl or O-heteroaryl, wherein aryl and heteroaryl are as defined below. The alkoxy and aroxy groups can be substituted as described above for alkyl.

The terms "amine" and "amino" are art-recognized and refer to both unsubstituted and substituted amines, e.g., a moiety that can be represented by the general formula: —$NR_9R_{10}$ or $NR_9R_{10}R'_{10}$, wherein $R_9$, $R_{10}$, and $R'_{10}$ each independently represent a hydrogen, an alkyl, an alkenyl, —$(CH_2)_m$—$R'_8$ or $R_9$ and $R_{10}$ taken together with the N atom to which they are attached complete a heterocycle having from 4 to 8 atoms in the ring structure; $R'_8$ represents an aryl, a cycloalkyl, a cycloalkenyl, a heterocycle or a polycycle; and m is zero or an integer in the range of 1 to 8. In some embodiments, only one of $R_9$ or $R_{10}$ can be a carbonyl, e.g., $R_9$, $R_{10}$ and the nitrogen together do not form an imide. In some embodiments, the term "amine" does not encompass amides, e.g., wherein one of $R_9$ and $R_{10}$ represents a carbonyl. In some embodiments, $R_9$ and $R_{10}$ (and optionally $R'_{10}$) each independently represent a hydrogen, an alkyl or cycloalkyl, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of $R_9$ and $R_{10}$ is an alkyl group.

The term "amido" is art-recognized as an amino-substituted carbonyl and includes a moiety that can be represented by the general formula —$CONR_9R_{10}$ wherein $R_9$ and $R_{10}$ are as defined above.

"Halogen", as used herein, refers to fluorine, chlorine, bromine, or iodine.

"Nitro", as used herein, refers to —$NO_2$.

"Sulfhydryl", as used herein, refers to —SH.

"Hydroxyl", as used herein, refers to —OH.

"Sulfonyl" as used herein, refers to —$SO_2$—.

The term "carbonyl" is art-recognized and includes such moieties as can be represented by the general formula —CO—$XR_{11}$, or —X—CO—$R'_{11}$, wherein X is a bond or represents an oxygen or a sulfur, and $R_{11}$ represents a hydrogen, an alkyl, a cycloalkyl, an alkenyl, an cycloalkenyl, or an alkynyl, $R'_{11}$ represents a hydrogen, an alkyl, a cycloalkyl, an alkenyl, an cycloalkenyl, or an alkynyl. Where X is an oxygen and $R_{11}$ or $R'_{11}$ is not hydrogen, the formula represents an "ester". Where X is an oxygen and $R_{11}$ is as defined above, the moiety is referred to herein as a carboxyl group, and particularly when $R_{11}$ is a hydrogen, the formula represents a "carboxylic acid". Where X is an oxygen and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R'_{11}$ is hydrogen, the formula represents a "thioformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aryloxy, substituted aryloxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

Compounds

Compounds that bind to vascular endothelial growth factor receptor (VEGFR) are disclosed herein. The compounds can contain a one or more VEGFR binding moieties and a linker. The compounds can also contain one or more VEGFR binding moieties, a linker, and one or more detectable moieties. The compounds can also contain one or more VEGFR binding moieties, a linker, and one or more therapeutic moieties. The compounds can also contain one or more VEGFR binding moieties, a linker, one or more detectable moieties, and one or more therapeutic moieties. In some embodiments, the detectable moiety can be the therapeutic moiety. The linker covalently couples the VEGFR binding moiety to the moiety. In some embodiments, the VEGFR compounds contain one VEGFR binding moiety. In some embodiments, the VEGFR compounds contain two, three, or more VEGFR binding moieties.

The general structure of the compounds disclosed herein can be represented as (VBM)x-L-(DTM)y, where VBM is a VEGFR binding moiety, L is a linker, DTM is a detectable moiety and/or a therapeutic moiety, x is an integer from 1 to 5 and y is an integer from 1-5. In preferred examples, the compounds disclosed herein can be represented as (VBM)$_2$-L, (VBM)$_3$-L, (VBM)$_4$-L, VBM-L-DTM, (VBM)$_2$-L-DTM, (VBM)$_3$-L-DTM, (VBM)$_2$-L-(DTM)$_2$, (VBM)$_2$-L-(DTM)$_3$, and VBM-L-(DTM)$_3$.

VEGFR Binding Moiety

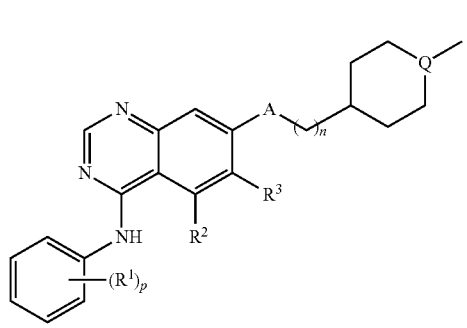

Formula A

Also, in the disclosed compounds n is preferably 1 or 2 and p is preferably 1 or 2.

In one example, the VEGFR binding moiety has Formula A-A, which correspond to vandetanib (ZD-G1).

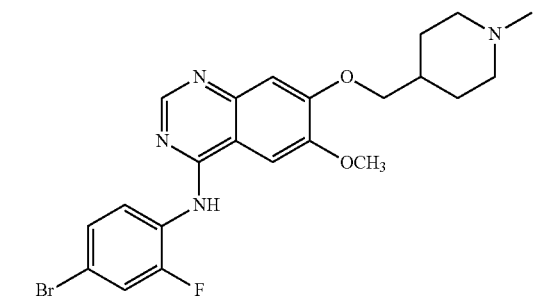 [SMILES: COc1cc2c(Nc3ccc(Br)cc3F)ncnc2cc1OCC1CCN(C)CC1]

In the disclosed compounds, two VEGF binding moieties can be coupled to a detectable moiety or therapeutic moiety (R$^6$) by a linker (L). Compounds with such a configuration are shown in Formula I:

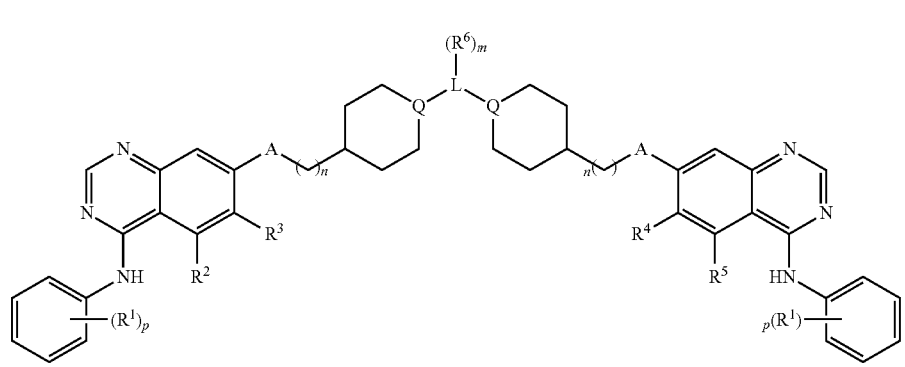

Formula I

The disclosed compounds can comprise one or more VEGF binding moieties. The VEGF binding moiety of the disclosed compounds can have a structure as shown in Formula A, where R$^1$ can be hydroxyl, halogen, C$_{1-3}$ alkyl, C$_{1-3}$ alkoxyl, C$_{1-3}$ alkanoyloxyl, trifluoromethyl, cyano, amino, or nitro;

R$^2$ and R$^3$ can be, independent of one another, hydrogen, hydroxyl, halogen, nitro, trifluoromethyl, cyano, C$_{1-3}$ alkyl, C$_{1-3}$ alkoxyl, C$_{1-3}$ alkylthio, or —NR$^7$R$^8$, wherein R$^7$ and R$^8$, which can be the same or different, each represents hydrogen or C$_{1-3}$ alkyl;

A can be oxygen, —CH$_2$—, —S—, —SO—, —SO$_2$—, —NR$^7$CO—, —CONR$^7$—, —SO$_2$NR$^7$—, —NR$^7$SO$_2$— or —NR$^7$—;

Q can be nitrogen or —CH—;

n is an integer from 1 to 5, for example, n can be 1, 2, 3, 4, or 5; and p is an integer from 1 to 4, for example, p can be 1, 2, 3, or 4.

In a preferred embodiment, of the VEGFR binding moiety, R$^1$ can be a halogen, for example, Br or F. In other examples, R$^1$ can be hydroxyl, C$_{1-3}$ alkyl, or C$_{1-3}$ alkyl.

In other examples R$^2$ is preferably hydrogen. In still other examples, R$^3$ is preferably C$_{1-3}$ alkyl, or C$_{1-3}$ alkyl. In yet further examples, A is preferably —O— and Q is preferably N.

wherein,

R$^1$ can be hydroxyl, halogen, C$_{1-3}$ alkyl, C$_{1-3}$ alkoxyl, C$_{1-3}$ alkanoyloxyl, trifluoromethyl, cyano, amino, or nitro;

R$^2$, R$^3$, R$^4$, and R$^5$ can be, independent of one another, hydrogen, hydroxyl, halogen, nitro, trifluoromethyl, cyano, C$_{1-3}$ alkyl, C$_{1-3}$ alkoxy, C$_{1-3}$ alkylthio, or —NR$^7$R$^8$, wherein R$^7$ and R$^8$, which can be the same or different, each represents hydrogen or C$_{1-3}$ alkyl;

A can be oxygen, —CH$_2$—, —S—, —SO—, —SO$_2$—, —NR$^7$CO—, —CONR$^7$—, —SO$_2$NR$^7$—, —NR$^7$SO$_2$— or —NR$^7$—;

Q can be nitrogen, or —CH—;

L is a linker;

R$^6$ contains a detectable moiety, a therapeutic moiety, or both;

n is an integer from 1 to 5, for example, n can be 1, 2, 3, 4, or 5;

m is an integer from 1 to 5, for example, m can be 1, 2, 3, 4, or 5; and p is an integer from 1 to 4, for example, p can be 1, 2, 3, or 4.

In some embodiments, the compound does not have Formula I where L is an aminosuberic or PEG linker and R$^6$ comprises 6-FAM (carboxyfluorescein).

The compound can have the Formula II, which correspond to Formula I, where A is oxygen, Q is nitrogen, n is 1, and R$^2$ and R$^5$ are both hydrogen:

Formula II

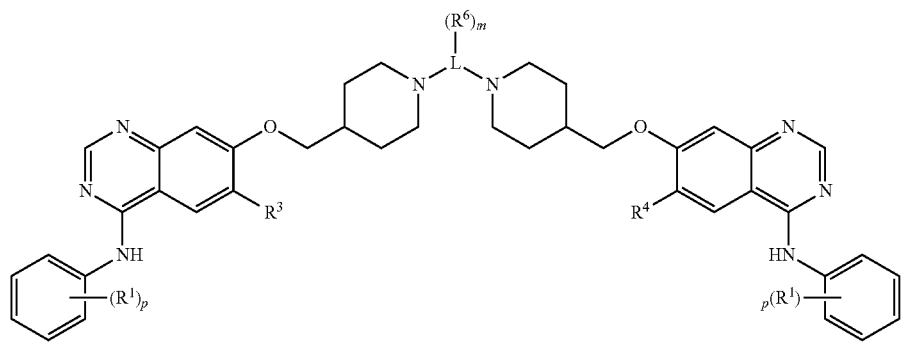

wherein, $R^1$ can be hydroxyl, halogen, $C_{1-3}$ alkyl, $C_{1-3}$ alkoxyl, $C_{1-3}$ alkanoyloxyl, trifluoromethyl, cyano, amino or nitro;

$R^3$ and $R^4$ can be, independent of one another, hydrogen, hydroxyl, halogen, nitro, trifluoromethyl, cyano, $C_{1-3}$ alkyl, $C_{1-3}$ alkoxyl, $C_{1-3}$ alkylthio, or $-NR^7R^8$, wherein $R^7$ and $R^8$, which can be the same or different, each represents hydrogen or $C_{1-3}$ alkyl;

L is a linker;

$R^6$ contains a detectable moiety, a therapeutic moiety, or both;

m is an integer from 1 to 5, for example, m can be 1, 2, 3, 4, or 5; and p is an integer from 1 to 4, for example 1, 2, 3, or 4.

In some embodiments, the compounds have Formula III:

wherein, $R^1$ can be hydroxyl, halogen, $C_{1-3}$ alkyl, $C_{1-3}$ alkoxyl, $C_{1-3}$ alkanoyloxyl, trifluoromethyl, cyano, amino, or nitro;

$R^2$ and $R^3$ can be, independent of one another, hydrogen, hydroxyl, halogen, nitro, trifluoromethyl, cyano, $C_{1-3}$ alkyl, $C_{1-3}$ alkoxyl, $C_{1-3}$ alkylthio, or $-NR^7R^8$ (wherein $R^7$ and $R^8$, which can be the same or different, each represents hydrogen or $C_{1-3}$ alkyl);

A can be oxygen, $-CH_2-$, $-S-$, $-SO-$, $-SO_2-$, $-NR^7CO-$, $-CONR^7-$, $-SO_2NR^7-$, $-NR^7SO_2-$, or $-NR^7-$;

Formula III

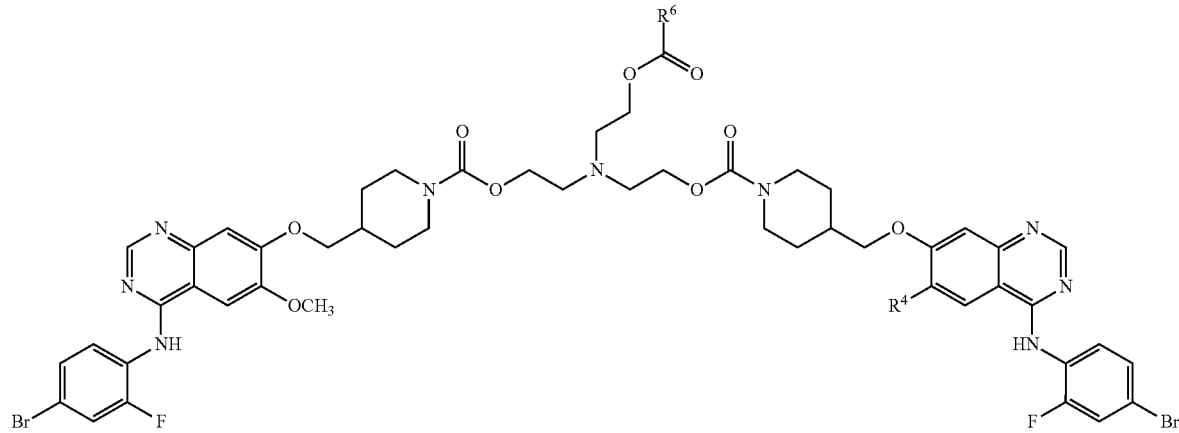

wherein, $R^6$ is a detectable moiety, a therapeutic moiety, or both.

Compounds of Formula IV are also described herein:

Formula IV

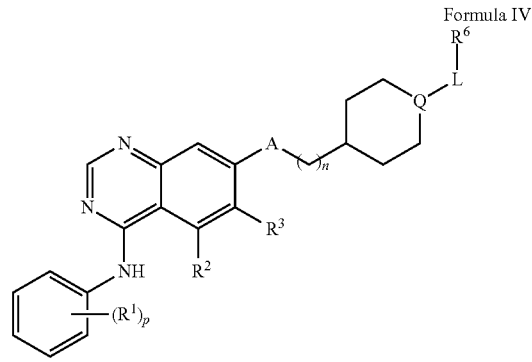

Q is nitrogen or $-CH-$;

L is a linker;

$R^6$ contains a detectable moiety, a therapeutic moiety, or both;

n is an integer from 1 to 5, for example, n can be 1, 2, 3, 4, or 5; and p is an integer from 1 to 4, for example, p can be 1, 2, 3, or 4.

In some embodiments, the compound is not Formula IV where L is an aminosuberic or PEG linker and $R^6$ comprises 6-FAM (carboxyfluorescein).

The compound can have Formula V:

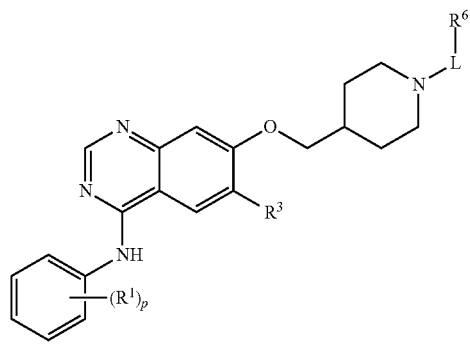

Formula V wherein,
$R^1$ can be hydroxyl, halogen, $C_{1-3}$ alkyl, $C_{1-3}$ alkoxyl, $C_{1-3}$ alkanoyloxyl, trifluoromethyl, cyano, amino, or nitro;
$R^3$ can be hydrogen, hydroxy, halogen, nitro, trifluoromethyl, cyano, $C_{1-3}$ alkyl, $C_{1-3}$ alkoxy, $C_{1-3}$ alkylthio, or $-NR^7R^8$, wherein $R^7$ and $R^8$, which can be the same or different, each represents hydrogen or $C_{1-3}$ alkyl;
L is a linker;
$R^6$ contains a detectable moiety, a therapeutic moiety, or both; and
p is an integer from 1 to 4, for example, p can be 1, 2, 3, or 4.

In some embodiments, the compounds have the following structure:

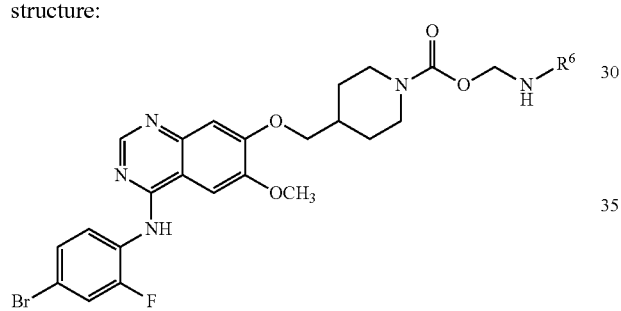

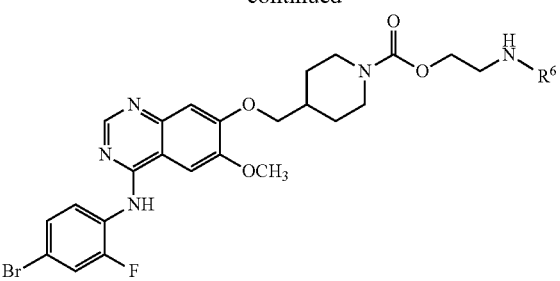

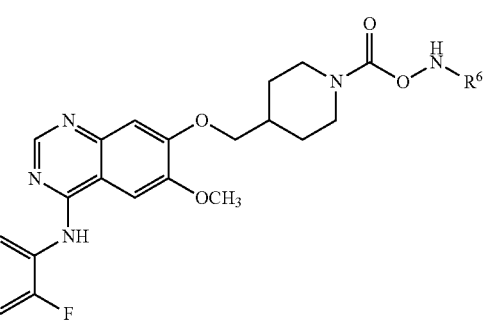

wherein $R^6$ contains a detectable moiety, a therapeutic moiety, or both.

In some examples of Formula I-V, $R_6$ can be a VEGFR ligand. When this ligand is a compound of Formula A, the compounds can be represented as Formula VI.

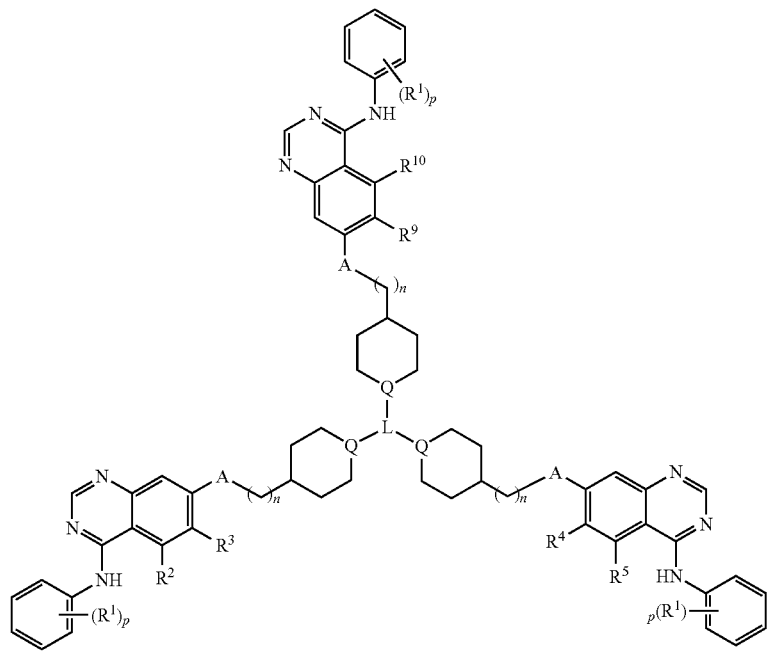

Formula VI wherein

R$^1$ can be hydroxyl, halogen, C$_{1-3}$ alkyl, C$_{1-3}$ alkoxyl, C$_{1-3}$ alkanoyloxyl, trifluoromethyl, cyano, amino, or nitro;

R$^2$, R$^3$, R$^4$, R$^5$, R$^9$ and R$^{10}$ can be, independent of one another, hydrogen, hydroxyl, halogen, nitro, trifluoromethyl, cyano, C$_{1-3}$ alkyl, C$_{1-3}$ alkoxy, C$_{1-3}$ alkylthio, or —NR$^7$R$^8$, wherein R$^7$ and R$^8$, which can be the same or different, each represents hydrogen or C$_{1-3}$ alkyl;

A can be oxygen, —CH$_2$—, —S—, —SO—, —SO$_2$—, —NR$^7$CO—, —CONR$^7$—, —SO$_2$NR$^7$—, —NR$^7$SO$_2$— or —NR$^7$—;

Q can be nitrogen, or —CH—;

L is a linker; such as NR$^{14}$R$^{15}$R$^{16}$ or (CH)R$^{14}$R$^{15}$R$^{16}$, wherein R$^{14}$, R$^{15}$, and R$^{16}$ are each bonded to a Q, and are each independently selected from the group consisting of hydrogen, C$_1$-C$_{20}$ alkyl; C$_1$-C$_{20}$ heteroalkyl; C$_1$-C$_{20}$ alkylamine; C$_1$-C$_{20}$ alkoxy; C$_1$-C$_{20}$ alkanoyloxy; or C$_1$-C$_{20}$ alkylamido;

wherein each R$^{14}$, R$^{15}$, and R$^{16}$ is optionally independently substituted with one or more substituents selected from the group consisting of halogen; hydroxyl; cyano; nitro; amino; alkylamino; dialkylamino; amido; alkylamido; =O; —S(O)$_2$; —SO—; —S—; —S(O)$_2$N—; haloalkyl; hydroxyalkyl; carboxy; alkoxyl; aryloxyl; alkoxycarbonyl; aminocarbonyl; alkylaminocarbonyl; and dialkylaminocarbonyl;

n is an integer from 1 to 5, for example, n can be 1, 2, 3, 4, or 5; and p is an integer from 1 to 4, for example, p can be 1, 2, 3, or 4.

In further examples, disclosed are compounds that have Formula VII:

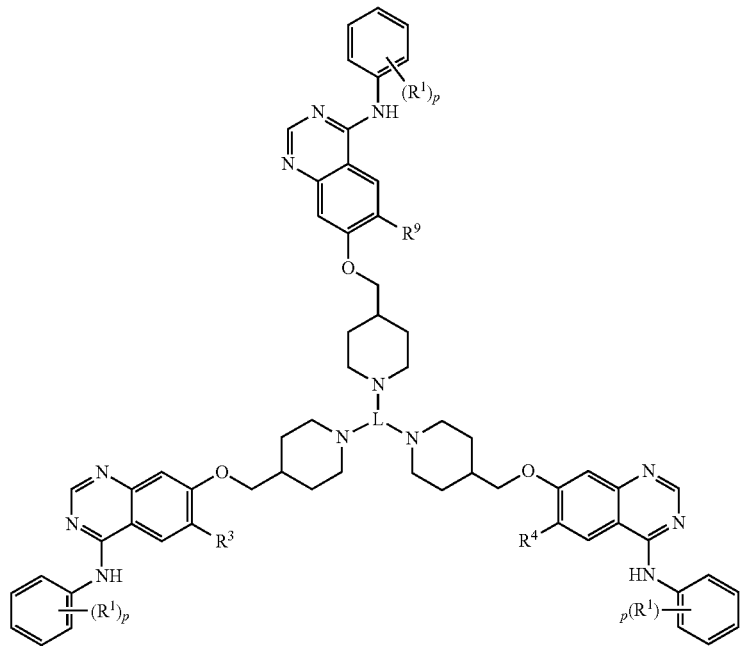

Formula VII wherein,

R$^1$ can be hydroxyl, halogen, C$_{1-3}$ alkyl, C$_{1-3}$ alkoxyl, C$_{1-3}$ alkanoyloxyl, trifluoromethyl, cyano, amino or nitro;

R$^3$, R$^4$, and R$^9$ can be, independent of one another, hydrogen, hydroxyl, halogen, nitro, trifluoromethyl, cyano, C$_{1-3}$ alkyl, C$_{1-3}$ alkoxyl, C$_{1-3}$ alkylthio, or —NR$^7$R$^8$, wherein R$^7$ and R$^8$, which can be the same or different, each represents hydrogen or C$_{1-3}$ alkyl;

L is a linker; and p is an integer from 1 to 4, for example 1, 2, 3, or 4.

In still further examples, the disclosed herein are compound having Formula VIII:

Formula VIII

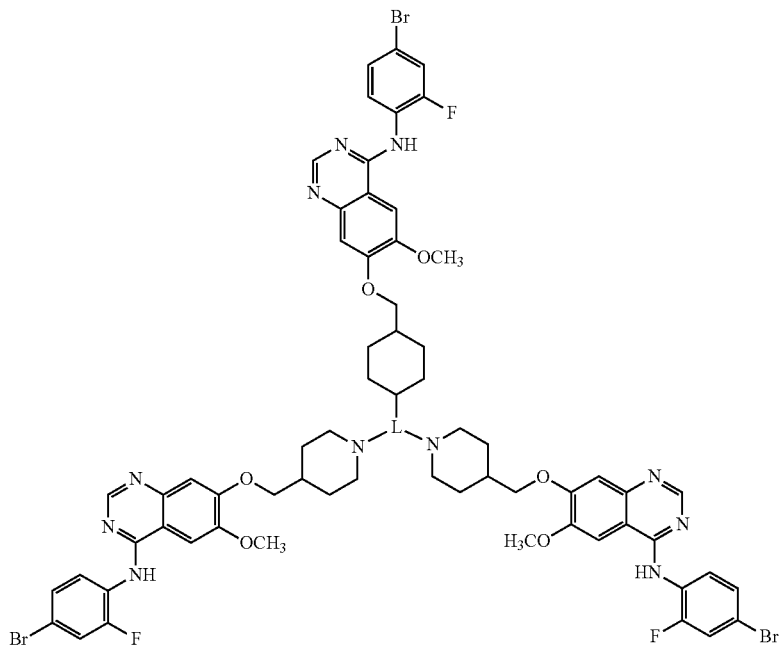

wherein L is a linker.

In a specific example, the compound can be ZD-G3.

Linker (L)

The compounds described herein contain a linker (L). The term "linker", as used herein, refers to one or more polyfunctional, e.g., bi-functional or tri-functional molecules, which can be used to covalently couple the one or more VEGFR binding moieties and the one or more detectable moieties of the disclosed compounds. The linker can be attached to any part of the VEGFR binding moiety so long as the point of attachment does not interfere with the biological activity, for example, the anti-tumor and/or anti-inflammatory activity of the compounds described herein.

The VEGFR binding moiety and the detectable moiety on the compounds are linked via a linker. The term "linker", as used herein, refers to one or more polyfunctional, e.g. bifunctional molecules or trifunctional molecules, which can be used to covalently couple the VEGFR binding moiety and the detectable moiety and which do not interfere with the properties of the VEGFR binding moiety and the detectable moiety in the compounds. The VEGFR binding moiety and the detectable moiety can be attached to any part of the linker. The linker can be attached to any part of the VEGFR binding moiety and the detectable moiety.

In some embodiments, the linker is flexible. In some embodiment, the linker is stable and biocompatible. In some embodiments, the covalent bond formed between the linker and the VEGFR binding moiety and/or the detectable moiety is stable. Stable, as used herein refers to a covalent bond that remains at least 70%, preferably at least 80%, more preferably at least 90% intact in aqueous solution at temperatures ranging from about 0° C. to about 100° C., at a pH ranging from about 2 to about 12, for at least 1 hour. The covalent bond formed between the linker and the VEGFR binding moiety and/or the detectable moiety is hydrolytically and reductively stable.

The linker can be a single atom, such as a heteroatom (e.g., O, N, or S), a group of atoms, such as a functional group (e.g., amine, —C(=O)—, —CH$_2$—), or multiple groups of atoms, such as an alkylene chain. Suitable linkers include but are not limited to oxygen, sulfur, carbon, nitrogen, alkyl, alkenyl, cycloalkyl, cycloalkenyl, heterocycloalkyl, alkoxyl, aryl, heteroaryl, ether, amine, diamine, amide, alkylamine, thioether, carboxylates, polymer, derivatives or combinations thereof.

The linker can be $R^{14}$, $C(O)R^{14}C(O)$, $C(O)OR^{14}OC(O)$, $C(O)R^{14}N$, $C(O)OR^{14}NH$, $NHR^{14}NH$, or $C(O)NHR^{14}NHC(O)$, $C(S)OR^{14}OC(S)$; wherein $R^{14}$ is O, S, $C_1$-$C_{20}$ alkyl; $C_1$-$C_{20}$ heteroalkyl; $C_1$-$C_{20}$ alkylamine; $C_1$-$C_{20}$ alkoxyl; $C_1$-$C_{20}$ alkanoyloxyl; or $C_1$-$C_{20}$ alkylamido, any of which can be optionally substituted with one or more substituents including halogen, alkoxyl, alkyl, alkenyl, cycloalkyl, cycloalkenyl, heterocycloalkyl, aryl, heteroaryl, amine, cyano, nitro, hydroxyl, carbonyl, acyl, carboxylic acid (—COOH), —C(O)$R^{12}$, —C(O)O$R^{12}$, carboxylate (—COO$^-$), primary amide (e.g., —CONH$_2$), secondary amide (e.g., —CONHR$^{12}$), —C(O)NR$^{12}$R$^{13}$, —NR$^{12}$R$^{13}$, —NR$^{12}$S(O)$_2$R$^{13}$, —NR$^{12}$C(O)R$^{13}$, —S(O)$_2$R$^{12}$, —SR$^{12}$, and —S(O)$_2$NR$^{12}$R$^{13}$, sulfinyl group (e.g., —SOR$^{12}$), and sulfonyl group (e.g., —SOOR$^{12}$);

wherein $R^{12}$ and $R^{13}$ can each independently be hydrogen, halogen, hydroxyl, alkyl, haloalkyl, alkenyl, alkynyl, cycloalkyl, heterocycloalkyl, aryl, heteroaryl, carbonyl, cyano, amino, alkylamino, dialkylamino, alkoxyl, aryloxyl, cycloalkyl, alkoxycarbonyl, aminocarbonyl, alkylaminocarbonyl, or dialkylaminocarbonyl.

In some embodiments, the linker is NR$^{14}$R$^{15}$R$^{16}$ or (CH)R$^{14}$R$^{15}$R$^{16}$; wherein the VEGF binding moiety or detectable moiety are bonded to at least one of R$^{14}$R$^{15}$R$^{16}$, and wherein R$^{14}$, R$^{15}$, and R$^{16}$ are each independently hydrogen, $C_1$-$C_{20}$ alkyl; $C_1$-$C_{20}$ heteroalkyl; $C_1$-$C_{20}$ alkylamine; $C_1$-$C_{20}$ alkoxy; $C_1$-$C_{20}$ alkanoyloxy; or $C_1$-$C_{20}$ alkylamido; any of which can be optionally substituted with one or more substituents independently selected from the group consisting of halogen; hydroxyl; cyano; nitro; amino; alkylamino; dialkylamino; amido; alkylamido; =O; —S(O)$_2$; —SO—;

—S—; —S(O)$_2$N—; haloalkyl; hydroxyalkyl; carboxy; alkoxy; aryloxy; alkoxycarbonyl; aminocarbonyl; alkylaminocarbonyl; and dialkylaminocarbonyl. For example, the linker is —(C(O)R$^{14}$)$_3$N, —(R$^{14}$)$_3$N, —(S(O)$_2$R$^{14}$)$_3$N, —(C(O)R$^{14}$)$_3$CH, —(R$^{14}$)$_3$CH, or —(S(O)$_2$R$^{14}$)$_3$CH. In some embodiment, C$_{1-20}$ refers to alkyl groups containing 1, 2, 3, 4, 5, 6, 7, 8, 9, 10, 11, 12, 13, 14, 15, 16, 17, 18, 19, or 20 carbons.

In some embodiments, the linker is —(CO—R$^{14}$)$_2$NH, —(R$^{14}$)$_2$NH, —(SO$_2$R$^{14}$)$_2$NH, —(SOR$^{14}$)$_2$NH, —(OR$^{14}$)$_2$NH, —(O—CO—R$^{14}$)$_2$NH, —(CO—O—R$^{14}$)$_2$NH, —(CO—R$^{14}$)$_2$CH$_2$, —(R$^{14}$)$_2$CH$_2$, —(SO$_2$R$^{14}$)$_2$CH$_2$, —(SOR$^{14}$)$_2$CH$_2$, —(O—CO—R$^{14}$)$_2$CH$_2$, or —(OR$^{14}$)$_2$CH$_2$.

Amino Acids

In some embodiments, the linker can be an amino acid. The amino acid can be a natural or non-natural amino acid. The term "non-natural amino acid" refers to an organic compound that is a congener of a natural amino acid in that it has a structure similar to a natural amino acid so that it mimics the structure and reactivity of a natural amino acid. The non-natural amino acid can be a modified amino acid, and/or amino acid analog, that is not one of the 20 common naturally occurring amino acids or the rare natural amino acids selenocysteine or pyrrolysine. Examples of suitable amino acids include, but are not limited to, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, a derivative, or combinations thereof.

Aminodicarboxylic Acids

In some embodiments, the linker is an amino dicarboxylic acid. In some embodiments, the amino dicarboxylic acid can have from 2 to 30 carbon atoms. Examples of suitable amino dicarboxylic acids include, but are not limited to, 1,6-dicarboxylic-2-amino hexanoic acid, 1,7-dicarboxylic-2-amino heptanoic acid, 1,8-dicarboxylic-2-amino octanoic acid, α-aminosuccinic acid, β-aminoglutaric acid, β-aminosebacic acid, 2,6-piperidine dicarboxylic acid, 2,5-pyrrole dicarboxylic acid, 2-carboxypyrrole-5-acetic acid, 2-carboxypiperidine-6-propionic acid, 2-aminoadipic acid, 3-aminoadipic acid, α-aminoazelaic acid, and 4-aminobenzene-1,3-dicarboxylic acid.

Dicarboxylic Acids and Derivatives

In some embodiments, the linker can be a dicarboxylic acid. In some embodiments, the dicarboxylic acid can have from 2 to 20 carbon atoms. Examples of dicarboxylic acid include, but are not limited to, butanedioic acid, pentanedioic acid, hexanedioic acid, heptanedioic acid, octanedioic acid, nonanedioic acid, decanedioic acid, undecanedioic acid, dodecanedioic acid, tridecanedioic acid, 1,12-dodecanedicarboxylic acid, 1,15-pentadecanedicarboxylic acid, hexadecanedioic acid, and 1,15-pentadecanedicarboxylic acid. In some embodiments, the dicarboxylic acid is an halogenated dicarboxylic acid, hydroxy dicarboxylic acid, or ether dicarboxylic acid.

Tricarboxylic Acids and Derivatives

In some embodiments, the linker can be a tricarboxylic acid or a derivative thereof. In some embodiments, the tricarboxylic acid can have from 2 to 30 carbon atoms. The tricarboxylic acid can be aliphatic or cyclic. Examples of tricarboxylic acid include, but are not limited to, 2-phosphonobutane-1,2,4-tricarboxylic acid and 1,2,3-propane tricarboxylic acid.

Alcohols

In some embodiments, the linker can be an alcohol or a derivative thereof. The alcohol can be a diol, triol, amino alcohol, amino dialcohol, amino trialcohol, ethylene glycol, propylene glycol, or a derivative. In some embodiments, the alcohol can have from 2 to 30 carbon atoms. Examples of suitable alcohols include, but are not limited to, triethanolamine, 2-aminoethanol, diisopropanolamine, triisopropanolamine, amino hexanol, 2-[(2-methoxyethyl)methylamino]-ethanol, propanolamine, N-methylethanolamine, diethanolamine, butanol amine, isobutanolamine, pentanol amine, 1-amino-3-(2-methoxyethoxy)-2-propanol, 2-methyl-4-(methylamino)-2-butanol, 6-amino-1-hexanol, heptaminol, isoetarine, norepinephrine, sphingosine, phenylpropanolamine, derivatives, and combinations thereof.

Polymers

In other embodiments, the linker can be a polymer. A wide variety of polymers and methods for forming the polymers are known in the art of polymer science. Polymers can be degradable or non-degradable polymers. Polymers can be natural or unnatural (synthetic) polymers. Polymers can be homopolymers or copolymers comprising two or more monomers. In terms of sequence, copolymers can be random, block, or comprise a combination of random and block sequences. The polymers can in some embodiments be linear polymers, branched polymers, or hyperbranched/dendritic polymers. The polymers can also be present as a crosslinked particle or surface functionalized inorganic particle. Suitable polymers include, but are not limited to, poly(vinyl acetate), copolymers of styrene and alkyl acrylates, and copolymers of vinyl acetate and acrylic acid, polyvinylpyrrolidone, dextran, carboxymethylcellulose, polyethylene glycol, polyalkylene, polyanhydrides, poly(ester anhydrides), polyhydroxy acids, such as polylactide (PLA), polyglycolide (PGA), poly(lactide-co-glycolide) (PLGA), poly-3-hydroxybutyrate (PHB), poly-4-hydroxybutyrate (P4HB), polycaprolactone, polyacrylates and polymethacrylates; polyanhydrides; polyorthoesters; polysytyrene (PS), poly(ethylene-co-maleic anhydride), poly(ethylene maleic anhydride-co-L-dopamine), poly(ethylene maleic anhydride-co-phenylalanine), poly(ethylene maleic anhydride-co-tyrosine), poly(butadiene-co-maleic anhydride), poly(butadiene maleic anhydride-co-L-dopamine) (pBMAD), poly(butadiene maleic anhydride-co-phenylalanine), poly(butadiene maleic anhydride-co-tyrosine), poly(bis carboxy phenoxy propane-co-sebacic anhydride) (poly (CCP:SA)), alginate; and poly(fumaric anhydride-co-sebacic anhydride (p[FA:SA]), copolymers of p[FA:SA], polyacrylates, and polyacrylamides, and copolymers thereof, and combinations thereof.

Other suitable linkers include, but are not limited to, diamino compounds such as ethylenediamine, 1,2-propylenediamine, 1,5-pentanediamine, 1,6-hexanediamine, and the like.

Detectable Moiety and/or Therapeutic Moiety (R$^6$)

The disclosed compounds can also contain one or more detectable moieties and/or one or more therapeutic moieties, R$^6$. In some embodiments, the detectable moiety can be the therapeutic moiety. The detectable moiety can contain any detectable label. Examples of suitable detectable labels include, but are not limited to, a UV-Vis label, a near-infrared label, a luminescent group, a phosphorescent group, a magnetic spin resonance label, a photosensitizer, a photocleavable moiety, a chelating center, a heavy atom, a radioactive isotope, a isotope detectable spin resonance label, a paramagnetic moiety, a chromophore, or any combination thereof. In some embodiment, the label is detectable without the addition of further reagents.

In some embodiments, the detectable moiety is a biocompatible detectable moiety, such that the compounds can be suitable for use in a variety of biological applications. "Biocompatible" and "biologically compatible", as used herein, generally refer to compounds that are, along with any metabolites or degradation products thereof, generally non-toxic to cells and tissues, and which do not cause any significant adverse effects to cells and tissues when cells and tissues are incubated (e.g., cultured) in their presence.

The detectable moiety can contain a luminophore such as a fluorescent label or near-infrared label. Examples of suitable luminophores include, but are not limited to, metal porphyrins; benzoporphyrins; azabenzoporphyrine; napthoporphyrin; phthalocyanine; polycyclic aromatic hydrocarbons such as perylene, perylene diimine, pyrenes; azo dyes; xanthene dyes; boron dipyoromethene, aza-boron dipyoromethene, cyanine dyes, metal-ligand complex such as bipyridine, bipyridyls, phenanthroline, coumarin, and acetylacetonates of ruthenium and iridium; acridine, oxazine derivatives such as benzophenoxazine; aza-annulene, squaraine; 8-hydroxyquinoline, polymethines, luminescent producing nanoparticle, such as quantum dots, nanocrystals; carbostyril; terbium complex; inorganic phosphor; ionophore such as crown ethers affiliated or derivatized dyes; or combinations thereof. Specific examples of suitable luminophores include, but are not limited to, Pd (II) octaethylporphyrin; Pt (II)-octaethylporphyrin; Pd (II) tetraphenylporphyrin; Pt (II) tetraphenylporphyrin; Pd (II) meso-tetraphenylporphyrin tetrabenzoporphine; Pt (II) meso-tetrapheny metrylbenzoporphyrin; Pd (II) octaethylporphyrin ketone; Pt (II) octaethylporphyrin ketone; Pd (II) meso-tetra(pentafluorophenyl)porphyrin; Pt (II) meso-tetra (pentafluorophenyl) porphyrin; Ru (II) tris (4,7-diphenyl-1,10-phenanthroline) (Ru (dpp)$_3$); Ru (II) tris (1,10-phenanthroline) (Ru(phen)$_3$), tris(2,2'-bipyridine)ruthenium (II) chloride hexahydrate (Ru(bpy)$_3$); erythrosine B; fluorescein; eosin; iridium (III) ((N-methyl-benzimidazol-2-yl)-7-(diethylamino)-coumarin)); indium (III) ((benzothiazol-2-yl)-7-(diethylamino)-coumarin))-2-(acetylacetonate); Lumogen dyes; Macroflex fluorescent red; Macrolex fluorescent yellow; Texas Red; rhodamine B; rhodamine 6G; sulfur rhodamine; m-cresol; thymol blue; xylenol blue; cresol red; chlorophenol blue; bromocresol green; bromcresol red; bromothymol blue; Cy2; a Cy3; a Cy5; a Cy5.5; Cy7; 4-nitrophenol; alizarin; phenolphthalein; o-cresolphthalein; chlorophenol red; calmagite; bromo-xylenol; phenol red; neutral red; nitrazine; 3,4,5,6-tetrabromphenolphtalein; congo red; fluorescein; eosin; 2',7'-dichlorofluorescein; 5(6)-carboxy-fluorescein; carboxynaphtofluorescein; 8-hydroxypyrene-1,3,6-trisulfonic acid; semi-naphthorhodafluor; semi-naphthofluorescein; tris (4,7-diphenyl-1,10-phenanthroline) ruthenium (II) dichloride; (4,7-diphenyl-1,10-phenanthroline) ruthenium (II) tetraphenylboron; platinum (II) octaethylporphyin; dialkylcarbocyanine; and dioctadecylcycloxacarbocyanine; derivatives or combinations thereof.

The detectable moiety can contain a radiolabel, also referred to herein as radioisotope. The radiolabel can also be a therapeutic moiety. i.e., a radiolabel comprising a therapeutic radionuclide such as, $^{90}$Y or $^{177}$Lu. Other examples of suitable radiolabels include, but are not limited to, metal $^{18}$F, $^{64}$Cu, $^{67}$Cu, $^{89}$Zr, $^{111}$In, $^{124}$I, $^{123}$I, and $^{99m}$Tc. In some embodiments, the radiolabel can be chelated by a macrocyclic molecule. Examples of such macrocyclic molecules include, but are not limited to, 2,2',2''-(10-(2-(2,5-dioxopyrrolidin-1-yl)oxy)-2-oxoethyl)-1,4,7,10-tetraazacyclododecane-1,4,7-triyl)triacetic acid (DOTA)-based chelators, diethylene triamine pentaacetic acid (DTPA)-based chelators, and a derivative or a combination thereof.

The detectable moiety can contain a magnetic spin resonance label. Examples of suitable spin resonance label include free radicals such as nitroxide-stable free radicals. Stable free radicals of nitroxides are known in the art, see for example Keana, "Newer Aspects of Synthesis and Chemistry of Nitroxide Spin Labels", Chemical Reviews, 1978, Vol. 78 No. 1, pp. 37-64, which disclosure is incorporated herein by reference. Suitable nitroxides include, but are not limited to, those derived from 2,2,6,6-tetramethylpiperidine-N-oxyl (TEMPO), 2,2,5,5-tetramethylpyrroline-N-oxyl, and 4,4-dimethyloxazolidine-N-oxyl which is a doxyl nitroxide. All of these compounds are paramagnetic and hence capable of excitation or changes in magnetic resonance energy levels and therefore provide imaging. Other nitroxides include, but are not limited to, doxyl nitroxides, proxyl nitroxides, azethoxyl nitroxides, imidazoline derived nitroxides, tetrahydrooxazine derived nitroxides, and the recently synthesized steroid nitroxides, and the like.

Spin labeling, as used herein, is understood to mean "spin label" as that is defined in the Keana article, namely when a nitroxide bearing molecule that is covalently attached to another molecule of interest, the nitroxide grouping does not significantly disturb the behavior of the system under study. Thus, the nitroxide molecule being paramagnetic, simply enhances the energy or excitation level subjected to the magnetic field during the magnetic resonance.

Therapeutic Moiety

The disclosed compounds can also contain a therapeutic moiety. The detectable moiety can be linked to a therapeutic moiety. Therapeutic moiety refers to a group that when administered to a subject, will cure, or at least relieve to some extent, one or more symptoms of, a disease or disorder. Therapeutic moiety include a wide variety of drugs, including antagonists, for example enzyme inhibitors, and agonists, for example a transcription factor which results in an increase in the expression of a desirable gene product (although as will be appreciated by those in the art, antagonistic transcription factors can also be used), are all included. In addition, therapeutic moiety includes those agents capable of direct toxicity and/or capable of inducing toxicity towards healthy and/or unhealthy cells in the body. Also, the therapeutic moiety can be capable of inducing and/or priming the immune system against potential pathogens. A number of mechanisms are possible including without limitation, (i) a radioisotope linked to a protein as is the case with a radiolabeled protein, (ii) an antibody linked to an enzyme that metabolizes a substance, such as a prodrug, thus rendering it active in vivo, (iii) an antibody linked to a small molecule therapeutic agent, (iv) a radioisotope, (v) a carbohydrate, (vi) a lipid, (vii) a thermal ablation agent, (viii) a photosensitizing agent, and (ix) a vaccine agent.

The therapeutic compound or moiety can be one that kills or inhibits cancer cells directly (e.g., cisplatin) or it can be one that can kill or inhibit a cancer cell indirectly (e.g., gold nanoparticles that kill or destroy cancer cells when heated using a light source). In one aspect, the compounds can include therapeutic moieties including without limitation small molecules or drugs. In some embodiments, the drug is doxorubicin. In some embodiments, doxorubicin can be substituted with a doxorubicin analog such as fluorescein.

The spectroscopic signature of fluorescein (UV absorbance (229 nm), visible absorbance (495 nm) and strong fluorescence (520 nm)) makes it an inexpensive and easy molecule to monitor. In some embodiments, the therapeutic moiety can comprise a targeting moiety, such as a peptide. In a specific example, the therapeutic moiety is a VEGFR ligand, such as vandetanib.

Pharmaceutical Compositions

The compounds described herein can be formulated for enteral, parenteral, topical, or pulmonary administration. The compounds can be combined with one or more pharmaceutically acceptable carriers and/or excipients that are considered safe and effective and can be administered to an individual without causing undesirable biological side effects or unwanted interactions. The carrier is all components present in the pharmaceutical formulation other than the active ingredient or ingredients.

The compounds described herein can be formulated for parenteral administration. "Parenteral administration", as used herein, means administration by any method other than through the digestive tract or non-invasive topical or regional routes. For example, parenteral administration can include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection, and by infusion.

Parenteral formulations can be prepared as aqueous compositions using techniques known in the art. Typically, such compositions can be prepared as injectable formulations, for example, solutions or suspensions; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof.

Solutions and dispersions of the active compounds can be prepared in water or another solvent or dispersing medium suitably mixed with one or more pharmaceutically acceptable excipients including, but not limited to, surfactants, dispersants, emulsifiers, pH modifying agents, viscosity modifying agents, and combination thereof.

Suitable surfactants can be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer™ 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation can also contain an antioxidant to prevent degradation of the active agent(s).

The formulation is typically buffered to a pH of 3-8 for parenteral administration. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above.

For parenteral administration, the compound can be incorporated into microparticles, nanoparticles, or combinations thereof. For example, the compound can be incorporated into polymeric microparticles.

Suitable oral dosage forms include tablets, capsules, solutions, suspensions, syrups, and lozenges. Tablets can be made using compression or molding techniques well known in the art.

Gelatin or non-gelatin capsules can prepared as hard or soft capsule shells, which can encapsulate liquid, solid, and semi-solid fill materials, using techniques well known in the art. Formulations can be prepared using a pharmaceutically acceptable carrier. As generally used herein "carrier" includes, but is not limited to, diluents, preservatives, binders, lubricants, disintegrators, swelling agents, fillers, stabilizers, and combinations thereof.

Suitable dosage forms for topical administration include creams, ointments, salves, sprays, gels, lotions, emulsions, and transdermal patches. The formulation can be formulated for transmucosal, transepithelial, transendothelial, or transdermal administration. The compounds can also be formulated for intranasal delivery, pulmonary delivery, or inhalation. The compositions can further contain one or more chemical penetration enhancers, membrane permeability agents, membrane transport agents, emollients, surfactants, stabilizers, and combination thereof.

Suitable classes of penetration enhancers are known in the art and include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocyclic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols). Examples of these classes are known in the art.

In one embodiment, the compounds are formulated for pulmonary delivery, such as intranasal administration or oral inhalation. The respiratory tract is the structure involved in the exchange of gases between the atmosphere and the blood stream. The lungs are branching structures ultimately ending with the alveoli where the exchange of gases occurs. The alveolar surface area is the largest in the respiratory system and is where drug absorbtion occurs. The alveoli are covered by a thin epithelium without cilia or a mucus blanket and secrete surfactant phospholipids. Carriers for pulmonary formulations can be divided into those for dry powder formulations and for administration as solutions. Aerosols for the delivery of therapeutic agents to the respiratory tract are known in the art. For administration via the upper respiratory tract, the formulation can be formulated into a solution, e.g., water or isotonic saline, buffered or unbuffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2. One skilled in the art can readily determine a suitable saline content and pH for an innocuous aqueous solution for nasal and/or upper respiratory administration.

The compounds described herein can be co-administered with one or more additional active agents, such as diagnostic agents, therapeutic agents, and/or prophylactic agents.

Methods of Making

The synthetic route for preparing compounds as disclosed herein is illustrated in Scheme 1. For example, the linker (e.g. compound 2) can be prepared by combining amino alcohol (e.g. compound 1) with carbonyldiimidazole in the presence of an alkyl amine (e.g. triethylamine). After the linker (2) is synthesized and the solvent removed, the VEGFR binding moiety (e.g. ZD-G1) can be linked to the linker by combining the VEGFR binding moiety (ZD-G1) to the linker (2). The detection moiety can then be linked to the linker. Alternatively, additional VEGFR binding moieties can be added to produce the trimer (ZD-G3). For example, the detection moiety can be linked to the linker via an amine group. This can be carried out by combining the amine (e.g. ethyl diamine) with the VEGFR-linker complex (compound 3) then conjugating a chelator (e.g. DOTA-NHS-ester) to the resulting complex to form for e.g. compound 4. A radiolabel (e.g. $^{64}$Cu) can then be chelated to compound 4 by combining compound 4 with a solution of the radiolabel (e.g. $^{64}$CuCl$_2$ in HCl and ammonium acetate). The synthesized compound can be purified by methods known to those of ordinary skill in the art, for. e.g., semipreparative radio-HPLC.

Scheme 1:

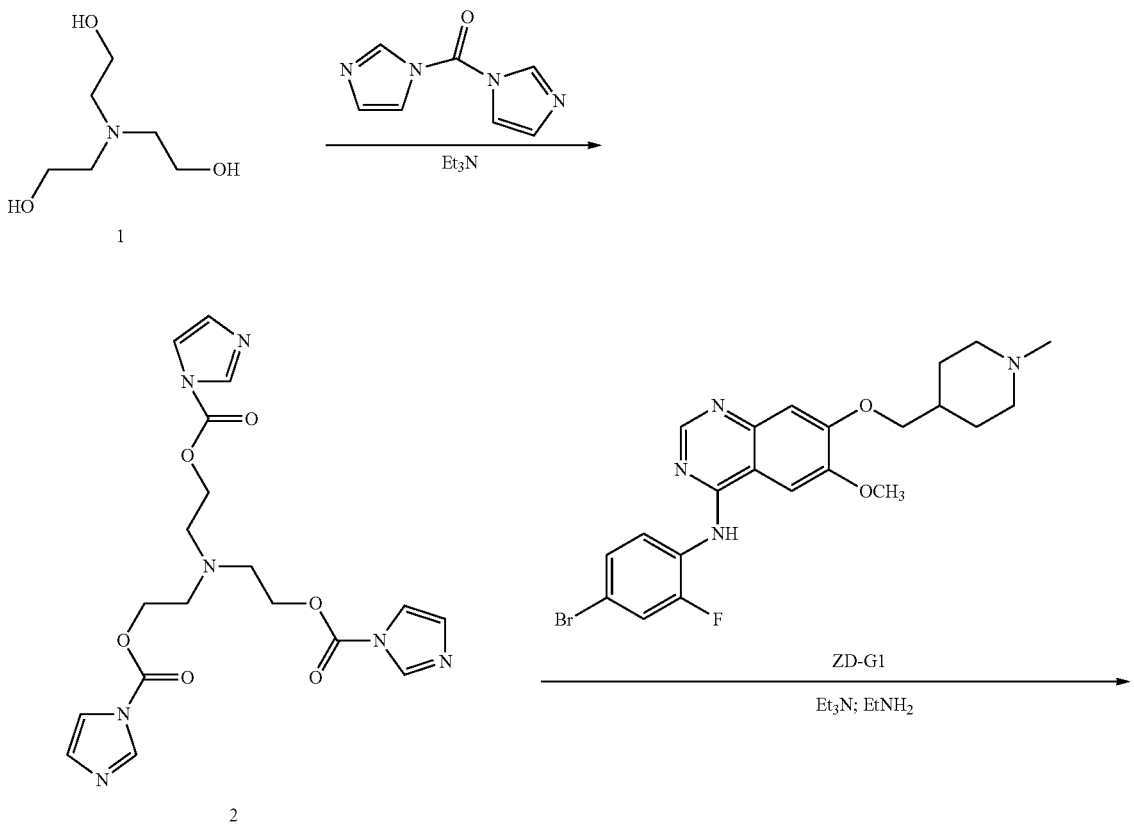

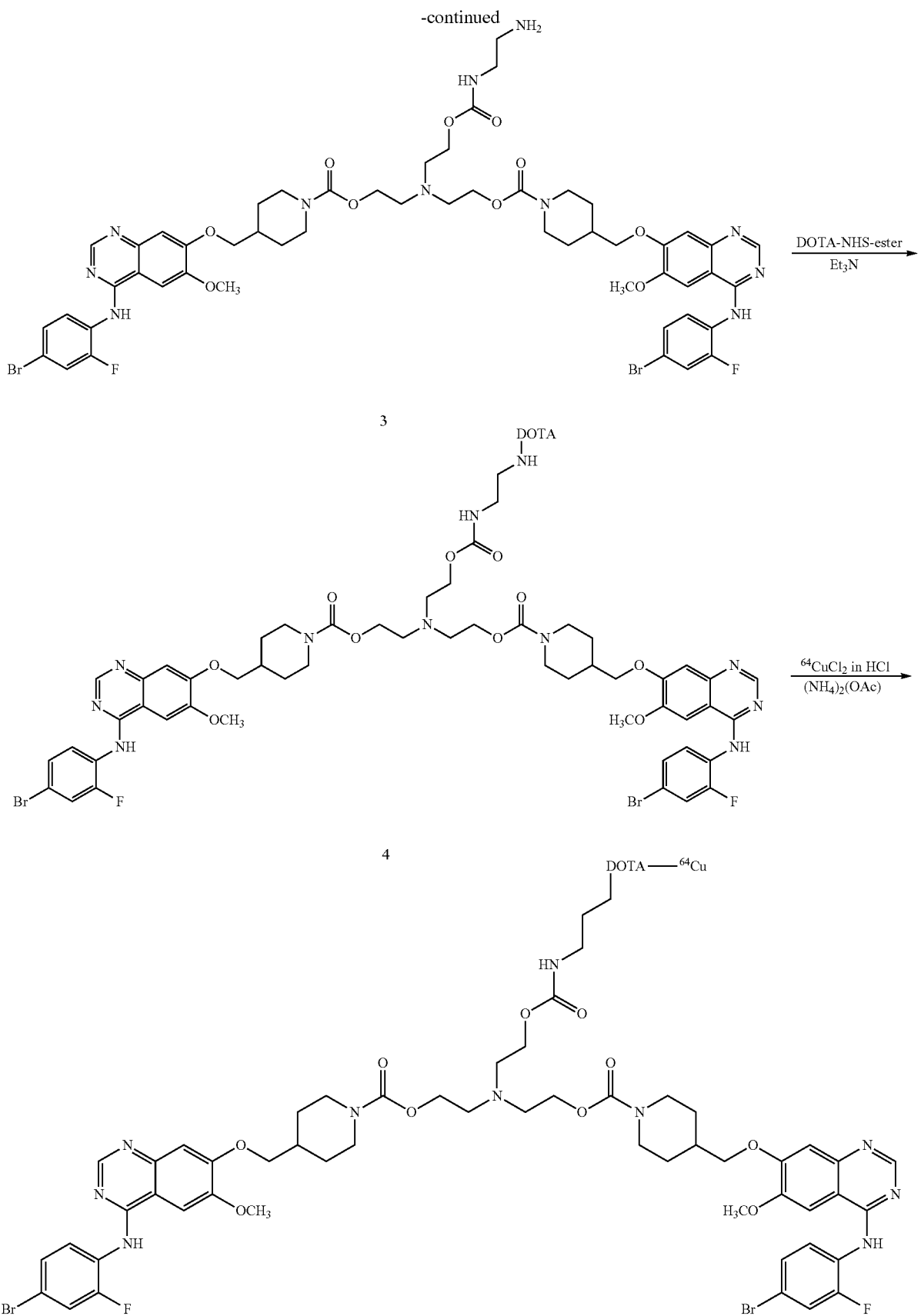

Other methods for coupling the VEGF binding moiety and detectible moiety to a linker are disclosed herein. The particular method will depend on the specific detectible moiety, VEGF binding moiety, and linker. Generally, the VEGF binding moiety can be treated with a linker that can form a bond with the VEGF binding moiety. That product can then be coupled with the detectable moiety. Alternatively, the linker and the detectible moiety can be coupled beforehand and then coupled with the VEGF binding moiety. Alternatively, the linker, VEGF binding moiety, and the detectible moiety can be coupled simultaneously.

Methods of Use

VEGF ligands (for e.g. VEGF A-D, and placenta growth factor (PLGF)), stimulate cellular responses by binding to tyrosine kinase receptors on the cell surface, known as VEGFR1 (Flt-1), VEGFR2 (Flk-1, KDR), and VEGFR3 (Flt-4). The VEGFR-1 and VEGFR-2 receptors are over expressed in a variety of tumors and are associated with advanced tumor growth and induction of tumor angiogenesis. For example, when VEGF ligands bind to VEGFR-1 and VEGFR-2, a tytosine kinase signaling cascade begins in endothelial cells that stimulate the production of factors that stimulate vessel permeability, proliferation/survival, migration, and finally differentiation into mature blood vessels. This is a fundamental step in the transition of tumors from a benign state to a malignant one.

In some embodiments, the compounds disclosed herein bind to VEGF receptors in VEGFR expressing cells. In some embodiments, the compounds bind to VEGFR2 in VEGFR2-expressing cells. The compounds can bind to VEGF receptors with a mean equilibrium dissociation constant ($K_d$) value from about 100 nM to about 0.01 nM, for e.g. about 95 nM, about 90 nM, about 85 nM, about 80 nM, about 75 nM, about 70 nM, about 65 nM, about 60 nM, about 55 nM, about 50 nM, about 45 nM, about 40 nM, about 35 nM, about 30 nM, about 25 nM, about 20 nM, about 15 nM, about 10 nM, about 9 nM, about 8 nM, about 8 nM, about 7 nM, about 6 nM, about 5 nM, about 4 nM, about 3 nM, about 2 nM, about 1 nM, about 0.9 nM, about 0.8 nM, about 0.7 nM, about 0.6 nM, about 0.5 nM, about 0.4 nM, about 0.3 nM, about 0.2 nM, about 0.1 nM, about 0.05 nM, about 0.01 nM, or about 44.7 nM or about 0.45 nM.

In some embodiments, the compounds disclosed can selectively inhibit the tyrosine kinase activity of VEGFR. In some embodiments, the compounds disclosed can selectively inhibit tyrosine kinase activity of VEGFR2. In some embodiments, the compounds disclosed can inhibit tyrosine kinase activity of VEGFR2 with 50% inhibitory concentration ($IC_{50}$) values of less than about 40 nM, about 35 nM, about 30 nM, about 25 nM, about 20 nM, about 19 nM, about 18 nM, about 17 nM, about 16 nM, about 15 nM, about 14 nM, about 13 nM, about 10 nM, about 9 nM, about 8 nM, about 7 nM, about 6 nM, about 5 nM, about 4 nM, about 3 nM, about 2 nM, about 1 nM, about 0.9 nM, about 0.8 nM, about 0.7 nM, about 0.6 nM, about 0.5 nM, about 0.4 nM, about 0.3 nM, about 0.2 nM, about 0.1 nM, about 0.09 nM, about 0.08 nM, about 0.07 nM, about 0.06 nM, about 0.05 nM, about 0.04 nM, about 0.03 nM, about 0.02 nM, about 0.01 nM, about 0.001 nM, about 0.0001 nM, or about 17.63 nM or about 0.023 nM. In some embodiments, the disclosed compounds can block VEGF-stimulated endothelial cell proliferation and migration. In some embodiments, the disclosed compounds can reduce tumor vessel permeability. In some embodiments, the disclosed compounds can be used to treat late-stage (metastatic) medullary thyroid cancer. In some embodiments, the disclosed compounds inhibit growth of experimental lung metastasis.

In some embodiments, the compounds disclosed can accumulate in VEGFR expressing cells post administration. The compounds can be administered via systemic administration, such as intravenous administration or subcutaneous administration, oral administration or by intratumoral injection. In some embodiments, the compounds disclosed can accumulate in VEGFR expressing cells, for example, tumor cells, within about 36 hours, about 48 hours, about 24 hours, about 23 hours, about 22 hours, about 20 hours, about 19 hours, about 18 hours, about 17 hours, about 16 hours, about 15 hours, about 14 hours, about 13 hours, about 12 hours, about 11 hours, about 10 hours, about 9 hours, about 8 hours, about 7 hours, about 6 hours, about 5 hours, about 4 hours, about 3 hours, about 2 hours, about 1.5 hours, about 1 hours, about 50 minutes, about 45 minutes, about 40 minutes, about 35 minutes, about 30 minutes, about 25 minutes, about 20 minutes, about 15 minutes, about 10 minutes, about 5 minutes post administration. In some embodiments, the VEGFR expressing cells, e.g., tumor cells exhibit sufficient uptake of the compounds disclosed, post administration. Sufficient, as used herein refers to uptake of the disclosed compounds into VEGFR expressing cells such that optical imaging of the VEGFR expressing cells exhibit low background noise. In some embodiments, the VEGFR expressing cells exhibit uptake of greater than about 5% ID/g, greater than about 4.7% ID/g, greater than about 4.5% ID/g, greater than about 4.3% ID/g, greater than about 4% ID/g, greater than about 3.7% ID/g, greater than about 3.5% ID/g, greater than about 3.3% ID/g, greater than about 3% ID/g, greater than about 2.7% ID/g, greater than about 2.5% ID/g, greater than about 2.3% ID/g, greater than about 2% ID/g, greater than about 1.8% ID/g, greater than about 1.5% ID/g, greater than about 1.3% ID/g, greater than about 1% ID/g, greater than about 0.9% ID/g, greater than about 0.8% ID/g, greater than about 0.6% ID/g, greater than about 0.5% ID/g, greater than about 0.4% ID/g, greater than about 0.3% ID/g, greater than about 0.2% ID/g, greater than about 0.1% ID/g, for example about 2. 7% ID/g, about 3.70% ID/g, about 3.8% ID/g, about 0.3% ID/g, about 0.7% ID/g, or about 0.5% ID/g of the disclosed compounds post administration.

Because of the high uptake of the compounds in VEGFR expressing cells, the compounds disclosed herein can be used to image VEGFR expression, for example, by confocal microscopic imaging, CT imaging, PET imaging, MRI, or any combination thereof. In some embodiments, the compounds disclosed can be used to image VEGFR expression in a disease. In some embodiments, the disclosed compounds can be used to image VEGF-stimulated endothelial cell proliferation and migration. In some embodiments, the disclosed compounds can be used to image tumor vessel permeability. In some embodiments, the disclosed compounds can be used to image late-stage (metastatic) medullary thyroid cancer. In some embodiments, the disclosed compounds can be used to image growth of experimental lung metastasis.

In some embodiments, non-targeted cells and/or tissues such as the kidney, muscles, heart, blood, lung, gastrointestinal tract, and/or spleen exhibit low uptake of the disclosed compounds. In some embodiments, uptake of the disclosed compounds in the non-targeted tissues such as the kidney is less than about 2.5% ID/g, less than about 2.3% ID/g, less than about 2% ID/g, less than about 1.8% ID/g, less than about 1.5% ID/g, less than about 1.3% ID/g, less than about 1% ID/g, less than about 0.9% ID/g, less than about 0.8%

ID/g, less than about 0.6% ID/g, less than about 0.5% ID/g, less than about 0.4% ID/g, less than about 0.3% ID/g, less than about 0.2% ID/g, or less than about 0.1% ID/g at about 24 hours, about 23 hours, about 22 hours, about 20 hours, about 19 hours, about 18 hours, about 17 hours, about 16 hours, about 15 hours, about 14 hours, about 13 hours, about 12 hours, about 11 hours, about 10, about 9 hours, about 8 hours, about 7 hours, about 6 hours, about 5 hours, about 4 hours, about 3 hours, about 2 hours, about 1.5 hour, about 1 hour, about 50 minutes, about 45 minutes, about 40 minutes, about 35 minutes, about 30 minutes, about 25 minutes, about 20 minutes, about 15 minutes, about 10 minutes, about 5 minutes post administration.

The ratio of compound uptake in the targeted cells to non-targeted cells, for example, tumor cells to muscle cells can be high. In some embodiments, the ratio of compound uptake in targeted cells to non-targeted cells, for example, tumor cells to muscle cells can be greater than 5, greater than 6, greater than 7, greater than 8, greater than 9, greater than 10, greater than 11, greater than 12, greater than 13, greater than 14, greater than 15, greater than 16, greater than 17, greater than 18, greater than 19, greater than 20, greater than 25, greater than 30, greater than 35, greater than 40, greater than 45, or greater than 50. The ratio of compound uptake in targeted cells to non-targeted cells can remain high for as long as about 2 hours, about 3 hours, about 4 hours, about 6 hours, about 10 hours, about 15 hours, about 18 hours, about 20 hours, about 24 hours, about 36 hours, about 46 hours, or as long as the compound is in a subject, post administration.

In one embodiment, the compounds disclosed herein exhibit rapid clearance from the blood. For example, in some embodiments, the liver exhibit high compound uptake at early time points of about 10 hours, about 9 hours, about 8 hours, about 7 hours, about 6 hours, about 5 hours, about 4 hours, about 3 hours, about 2 hours, about 1.5 hour, about 1 hour, about 50 minutes, about 45 minutes, about 40 minutes, about 35 minutes, about 30 minutes post administration. In these embodiments, the liver uptake can be about 20% ID/g, about 18% ID/g, about 15% ID/g, about 12% ID/g, about 10% ID/g, about 8% ID/g, or about 5% ID/g. As time progresses, the amount of compound in the liver is decreased to less than about 5% ID/g, less than about 4.7% ID/g, less than about 4.5% ID/g, less than about 4.3% ID/g, less than about 4% ID/g, less than about 3.7% ID/g, less than about 3.5% ID/g, less than about 3.3% ID/g, less than about 3% ID/g, less than about 2.7% ID/g, less than about 2.5% ID/g, less than about 2.3% ID/g, less than about 2% ID/g, less than about 1.8% ID/g, less than about 1.5% ID/g, less than about 1.3% ID/g, less than about 1% ID/g, less than about 0.9% ID/g, less than about 0.8% ID/g, less than about 0.6% ID/g, less than about 0.5% ID/g, less than about 0.4% ID/g, less than about 0.3% ID/g, less than about 0.2% ID/g, or less than about 0.1% ID/g at about 24 hours, about 23 hours, about 22 hours, about 20 hours, about 19 hours, about 18 hours, about 17 hours, about 16 hours, about 15 hours, about 14 hours, about 13 hours, about 12 hours, about 11 hours, about 10 hours post administration.

In some embodiments, the disclosed compounds exhibit good extravasations and diffusion into the extracellular space. In some embodiments, the disclosed compounds can selectively bind to tumor cells, can exhibit a high diffusion rate in fluids, can exhibit fast clearance from blood, and/or exhibit good metabolic stability compared to labeled-VEGFR antibodies.

Methods for detecting or imaging cells expressing vascular endothelial growth factor receptor (VEGFR) in a mammal are disclosed. In some embodiments, the method can noninvasively determine VEGFR expression levels, by optical imaging, in VEGFR expressing cells. In some embodiments, the method can be used to identify patients that respond to anti-angiogenic drug. In some embodiments, the method can be used to diagnose and monitor the proliferation and development of angiogenic tumors. The method comprise administering to the mammal one or more of the disclosed compound, in an amount and for a time sufficient to detect or image at least a population of the cells expressing VEGFR in the mammal to which the detectable moiety is bound. The detectable moiety can be identified by confocal microscopic imaging, CT imaging, PET imaging, MRI, or any combination thereof.

Methods for imaging a population of cells expressing VEGFR within or about the body of an animal are also disclosed. These methods comprise administering to the animal an amount of one or more of the disclosed compound for a time effective to image a population of cells expressing VEGFR within or about the body of the animal. In some embodiments, the population of cells expressing VEGFR includes cancer cells, tumor cells, hyperproliferative cells, or any combination thereof. In some embodiments, the animal is a human diagnosed with cancer.

Methods of treating or ameliorating a symptom of a disease, dysfunction, or abnormal condition in a mammal are disclosed. These methods comprise administering to the mammal one or more of the compounds disclosed herein in an amount, and for a time sufficient to treat or ameliorate the symptom of the disease, dysfunction, or abnormal condition in the mammal. The compounds can contain a detectable moiety and/or therapeutic moiety that kills or inhibits an infected, dysfunctional, or abnormal cell and/or tissue directly (e.g., cisplatin) or indirectly (e.g., radioisotope or gold nanoparticle that kill or destroy cells when irradiated with a light source). If the detectable and/or therapeutic moiety is one that kills or inhibits a cell or tissue indirectly, then the method further comprises a step of taking appropriate action to "activate" or otherwise implement the activity of the moiety. For example, the detectable/therapeutic moiety attached to the disclosed compounds can be a gold nanoparticle and following administration to the patient and binding of the compound to cancer cells, the nanoparticles are irradiated, e.g., using a laser light, to kill or destroy the nearby cancer cells. In some embodiments, the method involves image guided surgery using a compound comprising a detectable moieties to detect and resect cancer from a subject followed by the use of the same or a different compound to kill the remaining cancer cells.

The compounds disclosed herein contain an effective amount of the one or more of the compounds disclosed. The amount to be administered can be readily determined by the attending physician based on a variety of factors including, but not limited to, age of the patient, weight of the patient, disease or disorder to be imaged or treated, and presence of a pre-existing condition, and dosage form to be administered (e.g., immediate release versus modified release dosage form). Typically, the effective amount is from about 0.1 mBq/kg to about 200 mBq/kg (e.g., less than about 5 mBq/kg, less than about 10 mBq/kg, less than about 15 mBq/kg, less than about 20 mBq/kg, less than about 25 mBq/kg, less than about 30 mBq/kg, less than about 40 mBq/kg, less than about 50 mBq/kg, less than about 75 mBq/kg, less than about 100 mBq/kg, less than about 125 mBq/kg, less than about 150 mBq/kg, less than about 175 mBq/kg, less than about 200 mBq/kg. Dosages greater or less than this can be administered depending on the diseases or disorder to be treated or imaged.

The compounds disclosed herein can be administered in an effective amount to image or treat a variety of diseases and disorders including but not limited to, proliferative disorders (e.g., cancers), diabetes, psoriasis, rheumatoid arthritis, Kaposi's sarcoma, haemangioma, acute and chronic nephropathies, atheroma, arterial restenosis, autoimmune diseases, acute inflammation, ocular diseases with retinal vessel proliferation, diabetic retinopathy, macular degeneration, and angiosarcoma.

The disclosed compounds can be used for PET imaging of tumor VEGFR2 expression. Compounds with two or more VEGFR binding moieties have significantly increased VEGFR2 binding affinity compared with those compounds having only one VEGFR binding moiety. In the noninvasive small-animal PET imaging studies, $^{64}$Cu-DOTA-ZD-G2 showed rapid and good tumor uptake, low organs accumulations and quick liver washout, and good tumor-to-background contrast in U87MG xenograft. Overall, bivalency strategy has an efficient effect on the receptor-binding interaction and in vivo kinetics of $^{64}$Cu-DOTA-ZD-G2. The results indicate that the $^{64}$Cu-DOTA-ZD-G2 radio conjugate can be used to image tumor angiogenesis, select patient for antiangiogenic treatment, and monitor VEGFR2-targeted cancer therapy. Thus, disclosed herein are methods whereby the disclosed compounds, having a radiolabeled detectable moiety, are administered to an individual and then the individual is scanned to detect the presence, location, and/or concentration of the compound.

The disclosed compounds are particularly advantageous in treating and/or imaging the growth of primary and recurrent solid tumors. Exemplary cancers which can be treated and/or imaged include, but are not limited to, cancer of the skin, colon, uterine, ovarian, pancreatic, lung, bladder, breast, renal system, and prostate. Other cancers include, but are not limited to, cancers of the brain, liver, stomach, esophagus, head and neck, testicles, cervix, lymphatic system, larynx, esophagus, parotid, biliary tract, rectum, endometrium, kidney, and thyroid; including squamous cell carcinomas, adenocarcinomas, small cell carcinomas, gliomas, neuroblastomas, and the like. More particularly the compounds are expected to inhibit the growth of those primary and recurrent solid tumors which are associated with VEGF especially those tumors which are significantly dependent on VEGF for their growth and spread, including for example, certain tumors of the colon, breast, prostate, lung, vulva and skin.

The compounds described herein can also be used to treat or image metastatic cancer either in patients who have received prior chemo, radio, or biological therapy or in previously untreated patients. In one embodiment, the patient has received previous chemotherapy. The compounds can be administered using a variety of routes including systemic administration, such as intravenous administration or subcutaneous administration, oral administration or by intratumoral injection. The compounds disclosed can also be used for imaging in patients who have been rendered free of clinical disease by surgery, chemotherapy, and/or radiotherapy.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

All reagents and solvents were purchased from Sigma-Aldrich Chemicals (St. Louis, Mo., USA) and used without further purification unless otherwise stated. ZD6474 was purchased from FDU, INC. (Shanghai, China). DOTA was purchased from Macrocyclics (Dallas, Tex., USA). $^{64}$CuCl$_2$ was ordered from Washington University. Water was purified using a Milli-Q ultra-pure water system from Millipore (Milford, Mass., USA). Mouse monoclonal antibody against VEGF-R$_2$ (sc-6251) was purchased from Santa Cruz Biotechnology. Monoclonal antibody against Vinculin (V9131) was obtained from Sigma-Aldrich. Anti-mouse IgG peroxidase linked whole antibody (NXA931) was from GE Healthcare.

Example 1

Synthesis of Bivalent ZD6474 (ZD-G2)

Triethylamine (4.0 mL, 28 mmol) was added to a stirred solution of triethanolamine (0.45 g, 3 mmol) in anhydrous $CH_2Cl_2$ (50 mL). To this solution, 1,1'-carbonyldiimidazole (CDI, 4.06 g, 24 mmol) was added and the resulting mixture was stirred at room temperature for 12 h. The mixture was cooled to 0° C., then 50 mL water was added and kept stirring for 30 minutes. The water was separated and the organic layer was washed with ice-cold water (2×50 mL), brine (50 mL). The solvent was dried over MgSO$_4$, evaporated under reduced pressure, and dried under high vacuum to give intermediate 2,2',2"-nitrilotris(ethane-2,1-diyl) tris (1H-imidazole-1-carboxylate) (1.16 g, 2.69 mmol, 90%) as a colorless oil. $^1$H NMR (300 MHz, CDCl$_3$): 8.07 (s, 6H), 7.32 (t, 6H, J=1.5), 7.05 (m, 6H), 4.47 (t, 6H, J=5.7), 3.05 (d, 6H, J=5.7).

ZD-G1 (210 mg, 0.42 mmol) was added to a solution of 2,2',2"-nitrilotris(ethane-2,1-diyl) tris(1H-imidazole-1-carboxylate) (85 mg, 0.22 mmol) in DMSO (2 mL). Triethylamine (400 µL, 2.80 mmol) was added to this solution. After stirring overnight in the ambient temperature, 50 µL ethyl diamine was added and then kept stirring at room temperature for 24 hours to complete the reaction. The reaction was quenched by the adding of 20 µL trifluoroacetic acid (TFA). (FIG. 1) The purification of the crude product was carried out on a semipreparative reversed phase high-performance liquid chromatography (HPLC) system (Agilent 1200 series) and was performed on a Phenomenex Luna C18(2) column 100R (250×10.00 mm). The absorbance was monitored at 254 nm. The peak containing the ZD-G2 was collected, lyophilized and stored in the dark at −20° C. until use. $^1$H NMR (500 MHz, DMSO): 8.715 (s, 2H, Ph-NH), 7.963 (s, 2H), 7.796 (d, 2H, J=2), 7.786 (d, 2H, J=2), 7.796 (d, 2H, J=2), 7.547 (m, 4H), 7.502 (s, 1H, CONH), 7.265 (s, 2H), 4.272 (m, 6H, —OCH$_2$—), 4.058 (m, 10H), 3.975 (s, 6H, —OCH$_3$), 3.345 (m, 6H), 2.876 (m, 8H), 1.96 (s, 2 h, —NH$_2$), 2.095 (m, 2H), 1.824 (m, 4 h), 1.242 (m, 4 h). The MS spectrum of ZD-G2: m/z 1210.5 (100, [M$^+$H]$^+$, calcd 1209.92); 606.0 ([M+2H]$^{2+}$).

DOTA Conjugation and Radiolabeling

DOTA-NHS-Ester (3 mg, 6 µmol) was added to 0.5 ml of a 10 µmol/mL ZD-G2 DMSO solution (6 µmol), and then 50 µL triethylamine was added. The reaction mixture was stirred in the dark at ambient temperature overnight and then quenched by adding 200 μL of TFA. The crude product was purified by a semipreparative reversed-phase HPLC employing a Phenomenex Luna C-18 column (250 mm×10 mm). Fractions containing ZD-G2-DOTA were collected, lyophilized, redissolved in DMSO at a concentration of 10 μmol/mL, and stored in the dark at −20° C. until use. ZD-G1-DOTA was prepared using similar procedures described above. ZD-G1-DOTA and ZD-G2-DOTA were produced in 85% and 72% yields respectively. The purified ZD-G1-DOTA and ZD-G2-DOTA was characterized by ITMS-CESI mass spectroscopy (MS). MS (ZD-G1-DOTA, electrospray): m/z 847.3 ($[M+H]^+$, calculated 846.27); 424.3 ($[M+2H]^{2+}$). MS (ZD-G2-DOTA, electrospray): m/z 1596.32 ($[M+H]^+$, calculated 1596.3); 789.6 ($[M+2H]^{2+}$).

ZD-G2-DOTA and ZD-G1-DOTA was radiolabeled using procedures known in the art. Briefly, 185 MBq (5 mCi) $^{64}CuCl_2$ in 0.1 M HCl was diluted by adding 300 μL 0.1 M ammonium acetate (pH 5.6). ZD-G1-DOTA or ZD-G2-DOTA (10 μmol/mL, 100 nmol) in 700 μL of 0.1 M ammonium acetate was mixed with 1-5 mCi of $^{64}Cu(OAc)_2$. The mixture was vortexed and incubated at 50° C. for 1 h. $^{64}Cu$ labeled compound was purified by semipreparative radio-HPLC, and the collected fraction containing $^{64}Cu$-DOTA-ZD-G2 or $^{64}Cu$-DOTA-ZD-G1 was evaporated and reconstituted in PBS, which was filtered into a sterile dose vial for use in animal experiments by passing through a 0.22 μm Millipore filter. The radiochemical yield and chemical purity were determined by HPLC. $^{64}Cu$-DOTA-ZD-G1 and $^{64}Cu$-DOTA-ZD-G2 (FIG. 1) were obtained in 80%-90% decay-corrected yield with radiochemical purity of more than 98%. The stability of $^{64}Cu$-DOTA-ZD-G1 and $^{64}Cu$-DOTA-ZD-G2 (370 KBq/100 μL) was also evaluated by incubating with Dulbecco's modified Eagle's medium (DMEM) containing 10% fetal bovine serum (FBS) at 37° C. for up to 24 h. Aliquots at 2 h, 6 h and 24 h were analyzed by HPLC and radio-TLC.

The specific activity of $^{64}Cu$-DOTA-ZD-G1 and $^{64}Cu$-DOTA-ZD-G2 was estimated to 1.7-2.3 MBq/nmol. The radio-HPLC analysis indicated that no change in the spectrum was found after 24 h incubation, indicating that both radiotracers were stable in DMEM (10% FBS) for up to 24 h at 37° C.

Cell Lines and Animal Model

U87MG human glioblastoma cells, MDA-MB-231 human breast cancer cells, and Hela cells were purchased from the American Type Culture Collection (ATCC, Manassas, Va.) and cultured in DMEM medium (Invitrogen, CA) with 10% fetal bovine serum at 37° C. with 5% $CO_2$. Human Umbilical Vein Endothelial (HUVEC) cells were purchased from PromCell (PromoCell GmbH, Sickingenstraβe 63/65, D-69126 Heidelberg, Germany) and cultured in Endothelial Cell Growth Medium (Ready-to-use, Promcell). Cells were used for in vitro and in vivo experiments when they reached ~75% confluence. All animal experiments were performed in compliance with the Guidelines for the Care and Use of Research Animals established by the Methodist Hospital Research Institute Animal Use Committee. Five-week-old female nude mice were purchased from Harlan (Indianapolis, Ind.). The U87MG xenograft model was generated by subcutaneous injection of 5×10$^6$ cells (suspended in 100 μL of PBS) into the left flank of mice. Three to four weeks after inoculation (tumor volume, 200-500 mm$^3$), the mice were used for PET imaging and biodistribution study.

Western Blot

Western blot was performed to determine the VEGFR2 expression using anti-VEGF-R2/Flk-1 antibody and anti-Vinculin antibody was used as the loading control. U87MG, MDA-MB-231, Hela, and HUVEC Cells were washed with ice-cold PBS (pH 7.4) and then lysed in the lysis buffer (Cell Signaling Technology) containing 25 mM Tris-HCl (pH 7.4), 150 mM NaCl, 1 mM EDTA, 1% NP-40, 5% glycerol supplemented with complete protease inhibitor cocktail (Thermo Scientific) on ice for 30 min. The lysates were centrifuged for 15 min at 4° C. and then the protein concentration was quantified using Pierce BCA protein assay kit (Thermo Scientific). The cell lysates (50 μg) were heated at 100° C. for 10 min in sample loading buffer (Thermo Scientific) and separated by SDS-PAGE (Thermo Scientific, Pierce). Proteins were transferred to polyvinylidene difluoride (PVDF, Bio-Rad). The membranes were blocked with 5% nonfat milk for 1 hr, probed with primary antibodies at 4° C. overnight and incubated with secondary antibody (GE Healthcare). Immunoreactive bands were visualized with a chemiluminescence detection system (Thermo Scientific, Pierce).

Cell Uptake and Blocking Assay

Figures 2A, 2B, 2C:
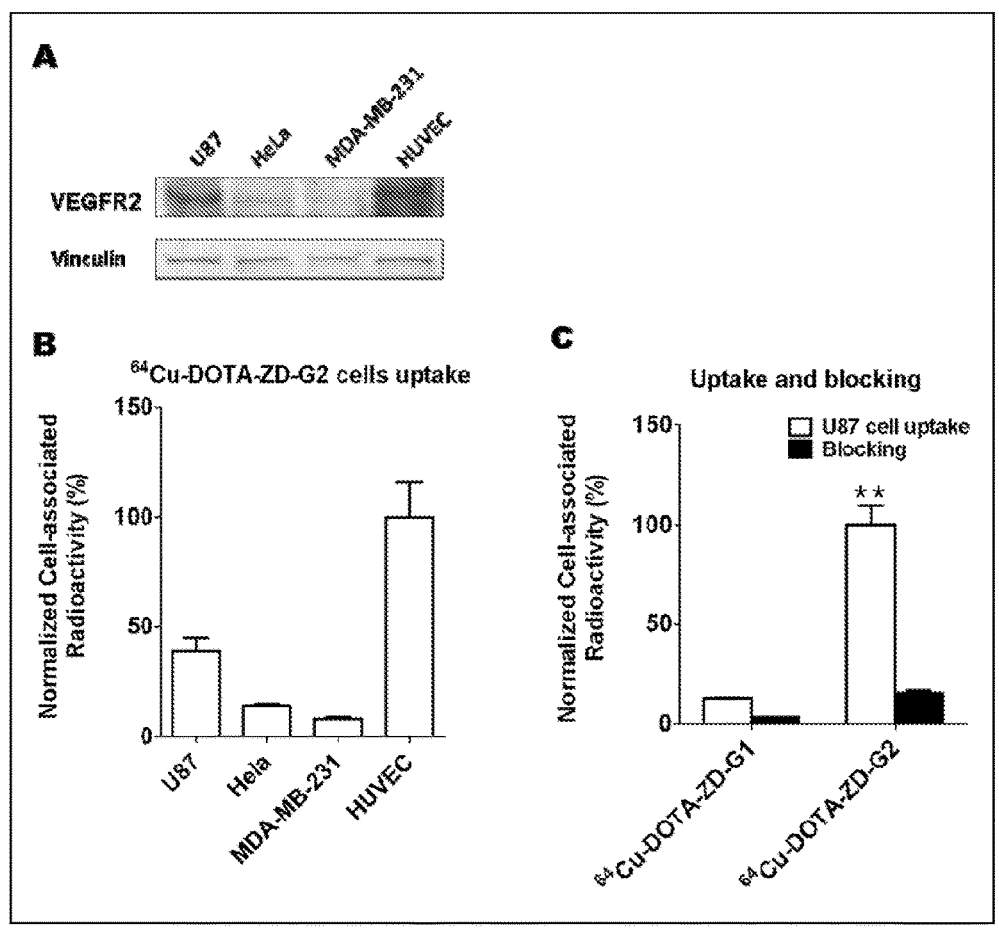
FIG. 2A is a comparative expression of VEGFR2 in four cell lines. VEGFR2 protein expression in cells was detected by Western blot analysis using anti-VEGF-R2/Flk-1 antibody. Anti-Vinculin antibody was used as the loading control.
FIG. 2B shows the binding of $^{64}$Cu-DOTA-ZD-G2 to cells with different levels of VEGFR2.
FIG. 2C shows a comparison of the cell binding of $^{64}$Cu-DOTA-ZD-G2 and $^{64}$Cu-DOTA-ZD-G1 in U87 cells and blocking experiment with non-radioactive ZDG2 and ZD-G1 respectively (n=3, **<0.0001).

The $^{64}Cu$-DOTA-ZD-G2 cell uptake assay was performed using U87MG, MDA-MB-231, Hela and HUVEC cells that express different numbers of VEGF receptors as demonstrated in western blot result (FIG. 2A). The day before the experiment, cells were seeded in 24 wells plate at concentration of 2×10$^5$ cells per mL. 37 KBq (1 μCi)$^{64}Cu$-DOTA-ZD-G2 was added to each well and incubated at 4° C. for 1 h. The cells were washed with ice-cooled PBS for three times, trypsinized and the cell-associated radioactivity was measured using a γ counter (Perkin-Elmer Packard, CT). The cell uptake and blocking assay of $^{64}Cu$-DOTA-ZD-G1 and $^{64}Cu$-DOTA-ZD-G2 was performed using U87 cells following the procedure described above. Briefly, KBq radiotracer $^{64}Cu$-DOTA-ZD-G1 or $^{64}Cu$-DOTA-ZD-G2 in 200 μL DMEM medium (non-FBS) were added to each well without or with 50-fold excess amount of nonradioactive ZD-G1 or ZD-G2 respectively. After incubating at 4° C. for 1 h, the cells were washed with ice-cooled PBS and trypsinized. The cell-associated radioactivity was measured using γ-counter (Perkin-Elmer Packard, CT).

As shown in FIG. 2A, HUVEC cells have high VEGFR2 expression, U87 cells have moderate VEGFR2 expression and MDA-MB-231 and Hela cells have low VEGFR2 expression. The radiotracer uptake level (FIG. 2B) shows uptake in HUVEC>U87>Hela and MDA-MB-231 cells, which is consistent with the western blot result. A comparison of $^{64}Cu$-DOTA-ZD-G1 and $^{64}Cu$-DOTA-ZD-G2 uptake using U87 cells is shown in FIG. 2C. The uptake of $^{64}Cu$-DOTA-ZD-G2 is 8 times more than $^{64}Cu$-DOTA-ZD-G1. Uptake of both $^{64}Cu$-DOTA-ZD-G2 and $^{64}Cu$-DOTA-ZD-G1 can be effective blocked by co-incubation with non-radioactive ZD-G2 and ZDG1, respectively.

Cell VEGFR2 Receptor-Binding Assay

VEGFR binding affinity and specificity of the $^{64}Cu$-DOTA-ZD-G1 or $^{64}Cu$-DOTA-ZDG2 were evaluated by saturation and displacement assays using U87 cells. Cells were seeded in 12 well plates at concentration of 5×10$^5$ cells per well the day before the experiment. For the receptor saturation analysis, the cells were incubated at 4° C. for 1 h with increasing concentration of $^{64}Cu$-DOTA-ZD-G1 or $^{64}Cu$-DOTA-ZD-G2 respectively. The cells were then washed with cold PBS and trypsinized. The cell-associated radioactivity was measured using γ-counter (Perkin-Elmer, CT) and the $K_d$ values were calculated by fitting the data by nonlinear regression using GraphPad Prism (GraphPad Software, CA). For the displacement/competition assay, cells were incubated with $^{64}Cu$-DOTA-ZD-G1 or $^{64}Cu$-DOTA- ZD-G2 and increasing concentration of non-radioactive ZD-G1 or ZD-G2 respectively. The experiment procedures are similar with those used for the saturation study described above. All experiments were carried out with triplicate samples.

Figures 3A, 3B, 3C:
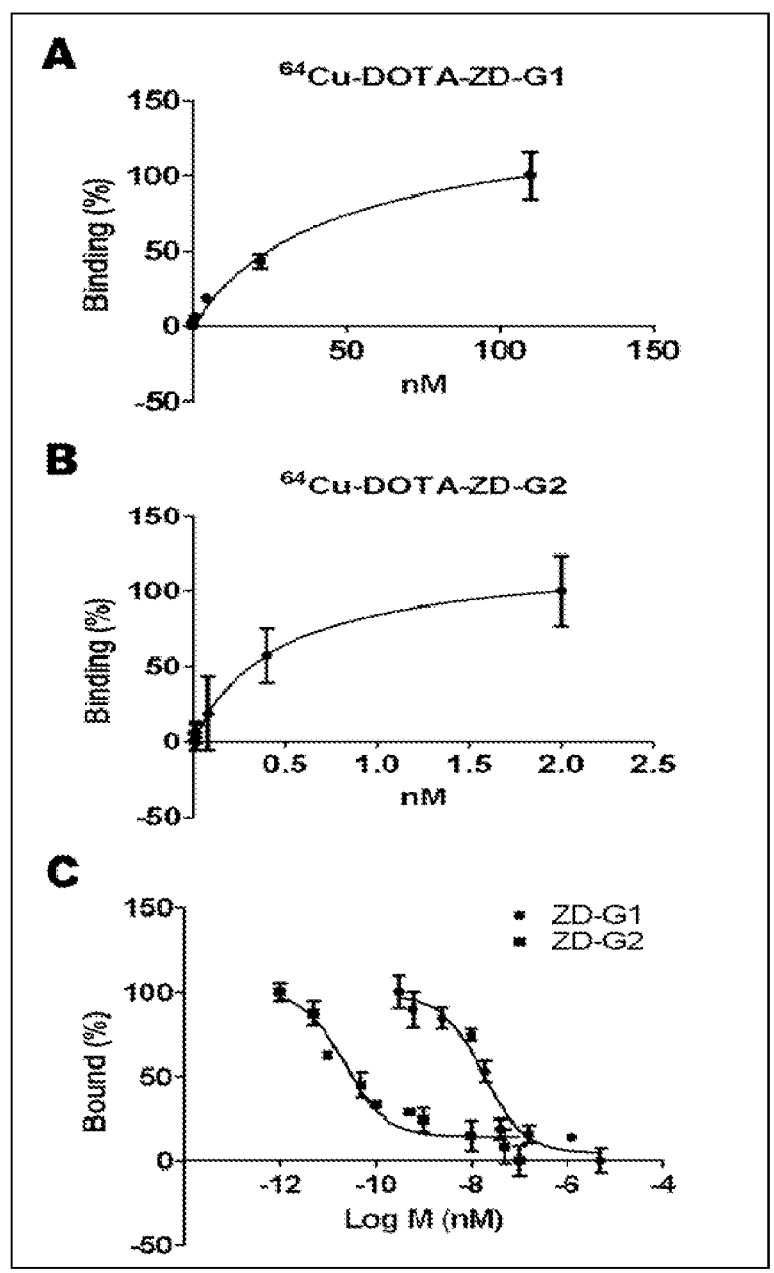
FIG. 3A is a graph showing representative saturation curve of $^{64}$Cu-DOTA-ZD-G1 bound to U87 cells (K$_d$: 44.75±15.04 nM).
FIG. 3B is a graph showing representative saturation curve of $^{64}$Cu-DOTA-ZD-G2 bound to U87 cells. (K$_d$: 0.45±0.32 nM).
FIG. 3C is a graph showing representative competition-binding curve of $^{64}$Cu-DOTA-ZD-G2 and $^{64}$Cu-DOTA-ZD-G1 to U87 cells (log of concentration of comparative compounds versus percent of the maximum specific binding of radiolabeled molecules).

The binding assay of the $^{64}$Cu-DOTA-ZD-G1 and $^{64}$Cu-DOTA-ZD-G2 to U87 cells yielded a mean equilibrium dissociation constant ($K_d$) value of 44.7 nM and 0.45 nM respectively. This is an indication that $^{64}$Cu-DOTA-ZD-G2 had 100-fold higher VEGFR2 avidity than $^{64}$Cu-DOTA-ZD-G1. The representative saturation curves of specifically bound $^{64}$Cu-DOTA-ZD-G1 and $^{64}$Cu-DOTA-ZD-G2 are shown in FIGS. 3A and 3B. Competition for binding between $^{64}$Cu-DOTA-ZD-G2 and non-radioactive ZD-G2 demonstrate that $^{64}$Cu-DOTA-ZD-G2 can be displaced by increasing amounts of unlabeled molecules (FIG. 3C). This provides evidence for receptor-mediated binding to VEGFR2-expressing cells. The similar competition result was also shown for the $^{64}$Cu-DOTA-ZD-G1. This experiment also demonstrated the 50% inhibitory concentration ($IC_{50}$) values for ZD-G1 and ZD-G2 were 17.63±1.2 nM and 0.023±0.002 nM respectively.

MicroPET Imaging

MicroPET/CT scans and image analysis were performed using a Siemens Inveon platform. Approximately 3.7 mBq $^{64}$Cu-DOTA-ZD-G1 or $^{64}$Cu-DOTA-ZD-G2 (100 µCi) was injected intravenously either without or with non-radioactive ZD-G1 or ZD-G2 (50 nmol, 60 µg/mouse) through a tail vein. Static PET scans were acquired at 2, 6 h, and 24 h post injection and standard CT scans were acquired in between the PET sessions. The images obtained were reconstructed using a two dimensional ordered-subsets expectation maximum (OSEM) algorithm and fused with the CT images with the Inveon Research Workplace (IRW). For each PET scan, regions of interest (ROIs) were drawn over the tumor and major organs on decay-corrected whole-body coronal images. The radioactivity concentration (accumulation) within tumor or organs was obtained from mean pixel values within the ROI volume and was converted to counts per milliliter per minute. Assuming a tissue density of 1 g/mL, the counts per milliliter per minute was converted to counts per gram per minute and then divided by the injected dose (ID) to obtain an imaging ROI derived percentage of the injected radioactive dose per gram of tissue (% ID/g).

Figures 4A, 4B:
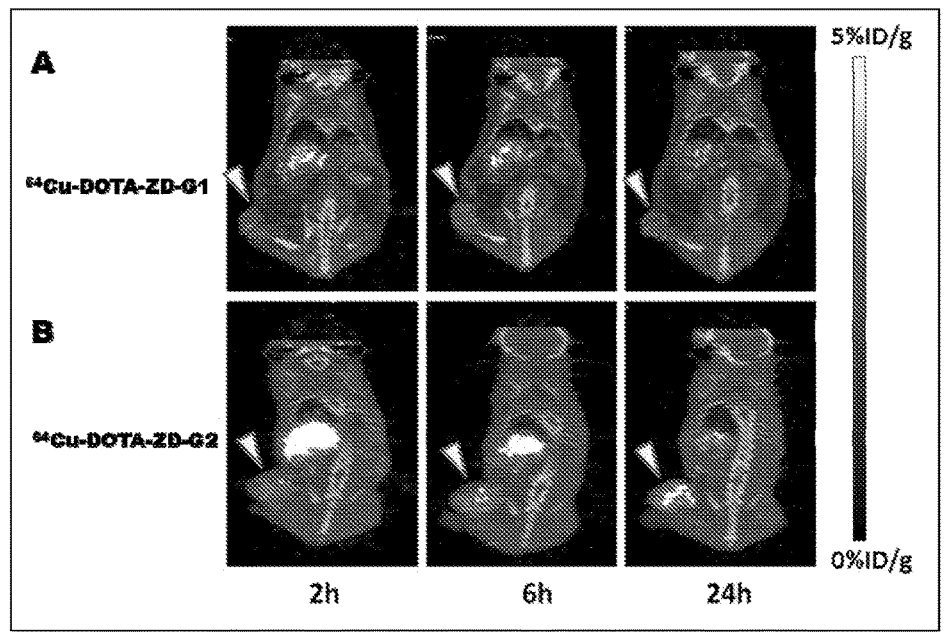
FIGS. 4A-4B show MicroPET/CT imaging of U87 tumor-bearing mice. Serial microPET/CT scans of U87 tumor-bearing mice injected intravenously with 3 to 4 MBq of $^{64}$Cu radiotracer $^{64}$Cu-DOTA-ZD-G1 (FIG. 4A) and $^{64}$Cu-DOTA-ZD-G2 (FIG. 4B).
Figures 5A, 5B, 5C:
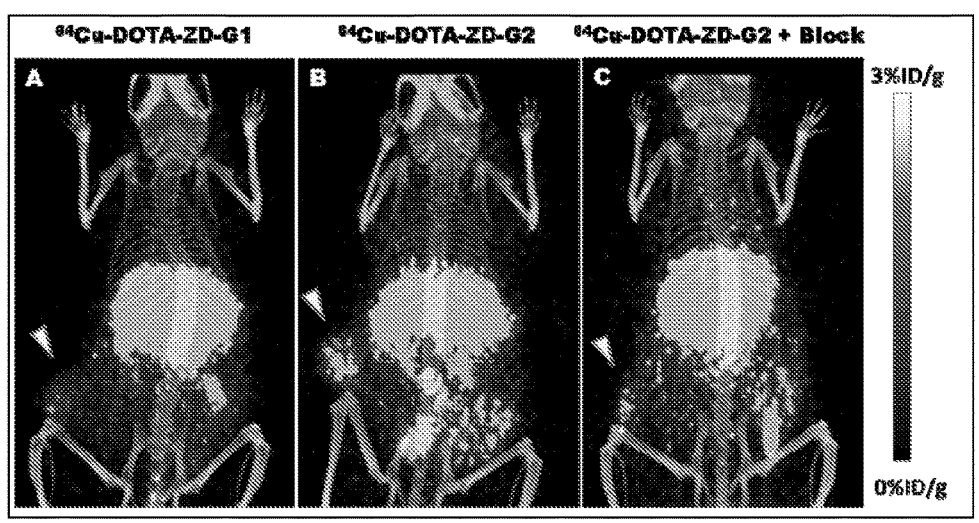
FIGS. 5A-5C show three-dimensional whole-body PET/CT images of U87MG tumor-bearing mice at 24 h post injection of $^{64}$Cu-DOTA-ZD-G1 (FIG. 5A), $^{64}$Cu-DOTA-ZD-G2 (FIG. 5B) and $^{64}$Cu-DOTA-ZD-G2 co-injected with 60 μg of ZD-G2 (FIG. 5C).
Figures 6A, 6B, 6C, 6D:
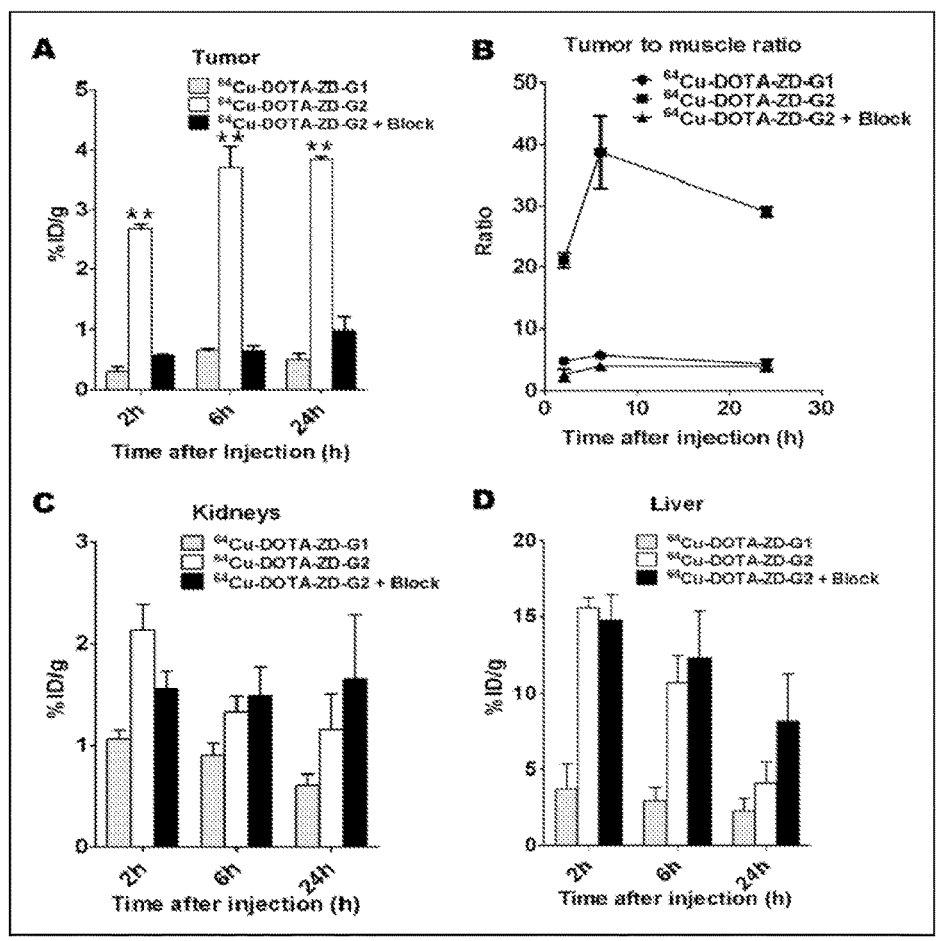
FIGS. 6A-6D show quantification analysis of the microPET scans. Comparison of decay corrected region-of-interest (ROI) analysis of $^{64}$Cu-DOTA-ZD-G1, $^{64}$Cu-DOTA-ZD-G2, and $^{64}$Cu-DOTA-ZD-G2 with co-injection of 60 μg of ZD-G2 in tumor (FIG. 6A), kidneys (FIG. 6C), and liver (FIG. 6D) (n≥3, **p<0.0001).

Multiple time point static microPET scans of $^{64}$Cu-DOTA-ZD-G1 and $^{64}$Cu-DOTA-ZDG2 were performed respectively using U87MG tumor bearing mice (n=3 per group). Representative decay-corrected coronal images at 2 h, 6 h and 24 h post injection are shown in FIG. 4. From the PET images, both radiotracers showed tumor accumulation as early as 2 h post injection. $^{64}$Cu-DOTA-ZD-G2 showed much higher tumor uptake than $^{64}$Cu-DOTA-ZD-G1 at all time points examined. From the ROI analysis as shown in FIG. 6A, tumor tissues uptake reached 2.67±0.08% ID/g at 2 h, 3.70±0.36% ID/g at 6 h, and 3.84±0.05% ID/g at 24 h post injection of $^{64}$Cu-DOTA-ZD-G2 and 0.29±0.09% ID/g at 2 h, 0.65±0.03% ID/g at 6 h, and 0.50±0.10% ID/g at 24 h post injection of $^{64}$Cu-DOTAZD-G1, resulting in more than 5 times higher tumor uptake. $^{64}$Cu-DOTA-ZD-G2 had high tumor to muscle uptake ratios as shown in FIG. 6B. $^{64}$Cu-DOTA-ZD-G2 exhibited high liver uptake at early time points with very low distribution in kidney and other tissues (FIGS. 6C and D). At 24 h post injection, liver uptake is decreased to 4.11±1.37% ID/g which is close to tumor uptake at 3.84±0.05% ID/g. To test the in vivo VEGFR specificity, blocking experiments were performed by co-injection of 50 nmol (60 µg/mouse) non-radioactive ZD-G2 with $^{64}$Cu-DOTA-ZD-G2. The tumor uptake was effectively reduced as shown in the PET images (FIG. 5) and the reduced tumor uptake values were 0.57±0.02% ID/g at 2 h, 0.65±0.08% ID/g at 6 h, and 0.98±0.23% ID/g at 24 h post injection, respectively (FIG. 6A). MicroPET result suggests that the bivalent radiotracer has increased binding to VEGFR and great improvement of in vivo tumor uptake.

Biodistribution Study

After the microPET/CT scans at 24 h after injection, the mice were immediately sacrificed to evaluate the distribution of the radiotracers in vivo. Blood, tumor, heart, lungs, liver, spleen, kidneys and muscle were collected and wet weighed. The radioactivity in each tissue was measured using a gamma counter (PerkinElmer, MA). Data are expressed as percent injected dose per gram of tissue (% ID/g). Blocking experiment was performed by coinjection of radiotracer with non-radioactive ZD-G1 or ZD-G2 (50 nmol, 60 µg/mouse).

Figure 7:
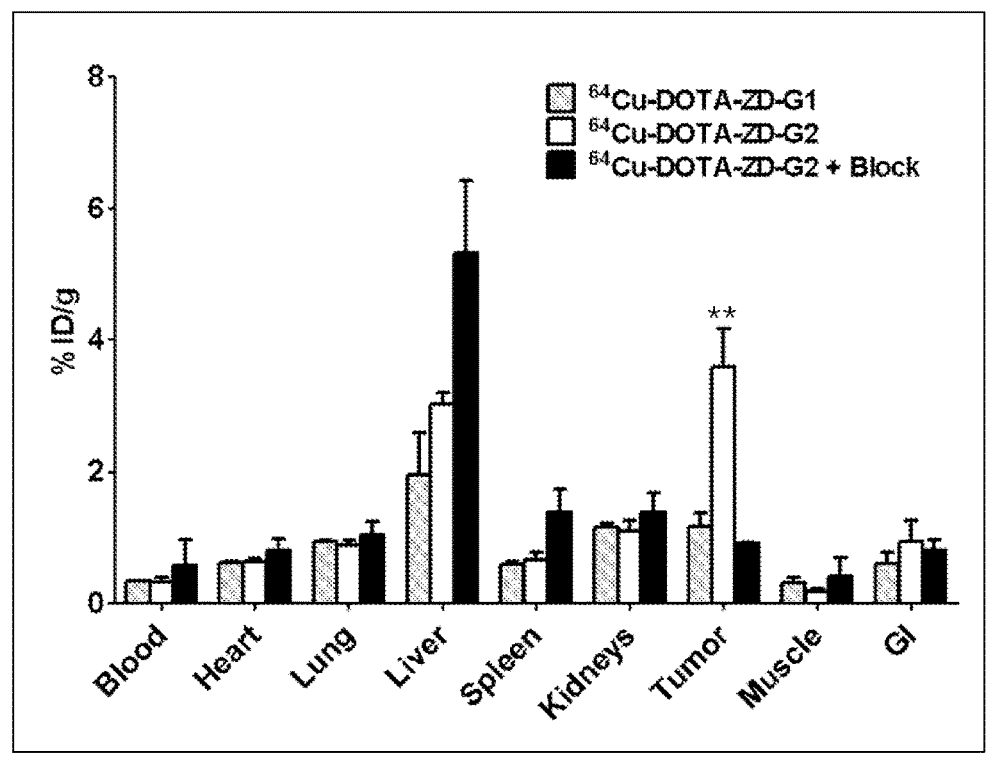
FIG. 7 is a bar graph showing biodistribution at 24 h post injection of $^{64}$Cu-DOTA-ZD G1, $^{64}$Cu-DOTA-ZDG2, and $^{64}$Cu-DOTA-ZD-G2 with co-injection of 60 μg of ZD-G2 in U87 tumor-bearing mice. Data shown represent mean±SD (**p<0.0001, n≥3 per group).

Because of the size effect and higher hydrophobic, uptake of $^{64}$Cu-DOTA-ZD-G2 was slightly higher than that of $^{64}$Cu-DOTA-ZD-G1 in most organs (FIG. 7). The tumor uptake of $^{64}$Cu-DOTA-ZD-G2 (3.59%±0.34% ID/g, n=3) is 4 times higher than that of $^{64}$Cu-DOTA-ZD-G1 (1.17±0.12% ID/g, n=3). The blocking study was performed as $^{64}$Cu-DOTA-ZD-G2 co-injected with 50 nmol of nonradioactive ZD-G2 and tumor uptake is decreased to 0.91±0.01% ID/g, which is 3 times lower compared with non-blocking mice. (p<0.0001) The excess amount of ZD-G2 successfully reduced the uptake of $^{64}$Cu-DOTA-ZD-G2 in the U87MG tumor, while the radioactivity in the kidney and all other dissected tissues was very close between with or without block compound except for liver. The uptake of $^{64}$Cu-DOTA-ZD-G1 in liver was 0.36 ID/g, n=3), whereas uptake was almost higher for $^{64}$Cu-DOTA-ZD-G2 (3.02±0.10% ID/g, n=3). This blocking effect confirms the VEGFR-binding specificity of the developed radiotracer $^{64}$Cu-DOTA-ZD-G2. The result obtained from biodistribution studies were consistent with the quantitative analysis of microPET imaging, which suggested that ROI analysis of noninvasive microPET scans was a true reflection of the biodistribution of $^{64}$Cu-DOTA-ZD-G2 in vivo.

Results Summary $^{64}$Cu labeled bivalent ZD-G2 conjugates and $^{64}$Cu-DOTA-ZD-G2 as a PET imaging probe for tumor VEGFR2 imaging based on clinical approved antiangiogenic drug ZD6474 (ZD-G1) were developed. The $^{64}$Cu-DOTA-ZD-G2 showed high VEGFR binding affinity and specificity as determined by in vitro cell assay and uptake/blocking assay, cell-saturation and competing assay. The binding affinity and specificity of this developed tracer was also confirmed in vivo by quantitative small-animal PET experiments and biodistribution studies.

Bivalent VEGFR2 targeting imaging probe from ZD6474 using triethanolamine backbone linker was developed. The linker length and rigidity can affect the multivalent ligand receptor interaction. In addition, the linkers used should have good physicochemical properties such as high stability and low toxicity. Triethanolamine is a suitable as a linker. Both of C-0 and C—N bonds are flexible, which can spin freely to change the angle between two parent compounds, which gives them more possibility to interact with the targeting receptor "pocket". At same time, N and O atoms in the linker structure can increase the water solubility of the bivalent complex. Additionally, triethanolamine has three arms in which two side chains have been used to build up bivalent structure, and the third arm can be used to conjugate with radiolabels for PET. Overall, the bivalent design with suitable length between linked two monomers, adjustable angle and proper hydrophilic greatly enhance the binding of bivalent compound comparing to its parent monomer.

Several in vitro assays to examine the interaction between $^{64}$Cu-DOTA-ZD-G2 and VEGFR2 were used. First, the cell uptake in four cell lines that express different level of VEGFR2 was tested. The cell uptake of $^{64}$Cu-DOTA-ZD-G2 was proportional to the VEGF receptor quantity in different cell lines (FIGS. 2A and B). $^{64}$Cu-DOTA-ZD-G2 had high uptake in U87 cells than $^{64}$Cu-DOTA-ZD-G1 and the decreased uptake of radiotracers in blocking study further proved the receptor-ligand specific interaction (FIG. 2C). Binding studies to U87 cells revealed a $K_d$ of 0.45 nM for $^{64}$Cu-DOTA-ZD-G2 and 44.7 nM for $^{64}$Cu-DOTA-ZD-G1, demonstrating a 100 time higher binding affinity for the developed bivalent compounds. Cell competition assay also proved the specific receptor-ligand binding of the radiotracers.

Considering the half-life of $^{64}$Cu (12.7 h), the PET imaging of $^{64}$Cu-DOTA-ZD-G2 and $^{64}$Cu-DOTA-ZD-G1 were acquired in 2 h, 6 h, and 24 h post injection (FIG. 4). Quantification of small animal PET images showed that $^{64}$Cu-DOTA-ZD-G2 had 5 times higher tumor uptake than that of $^{64}$Cu-DOTA-ZD-G1 (FIG. 6A). $^{64}$Cu-DOTAZD-G2 had clearly high tumor uptake at all time points and long tumor retention. The higher tumor uptake of $^{64}$Cu-DOTA-ZD-G2 can be attributed to higher VEGFR binding affinity, longer circulation time and slower tumor washout, compared with $^{64}$Cu-DOTAZD-G1. In addition, quantification of tumor-to-muscle ratio also showed the analogous result (FIG. 6B). $^{64}$Cu-DOTA-ZD-G2 have low kidney uptake at all time points, which is an advantage than reported radiolabeled VEGFR antibodies that usually have high kidney accumulation. The liver uptake of $^{64}$Cu-DOTA-ZD-G2 was high at 2 h post injection (15.3% ID/g) but was clear up quickly (4.1% ID/g at 24 h p.i.), which is favorable in PET imaging. The tumor uptake of $^{64}$Cu-DOTA-ZD-G2 could be effectively blocked by co-injection with non-radioactive ZD-G2, proving the in vivo ligand-tumor specific binding.

Example 2

Figure 8:
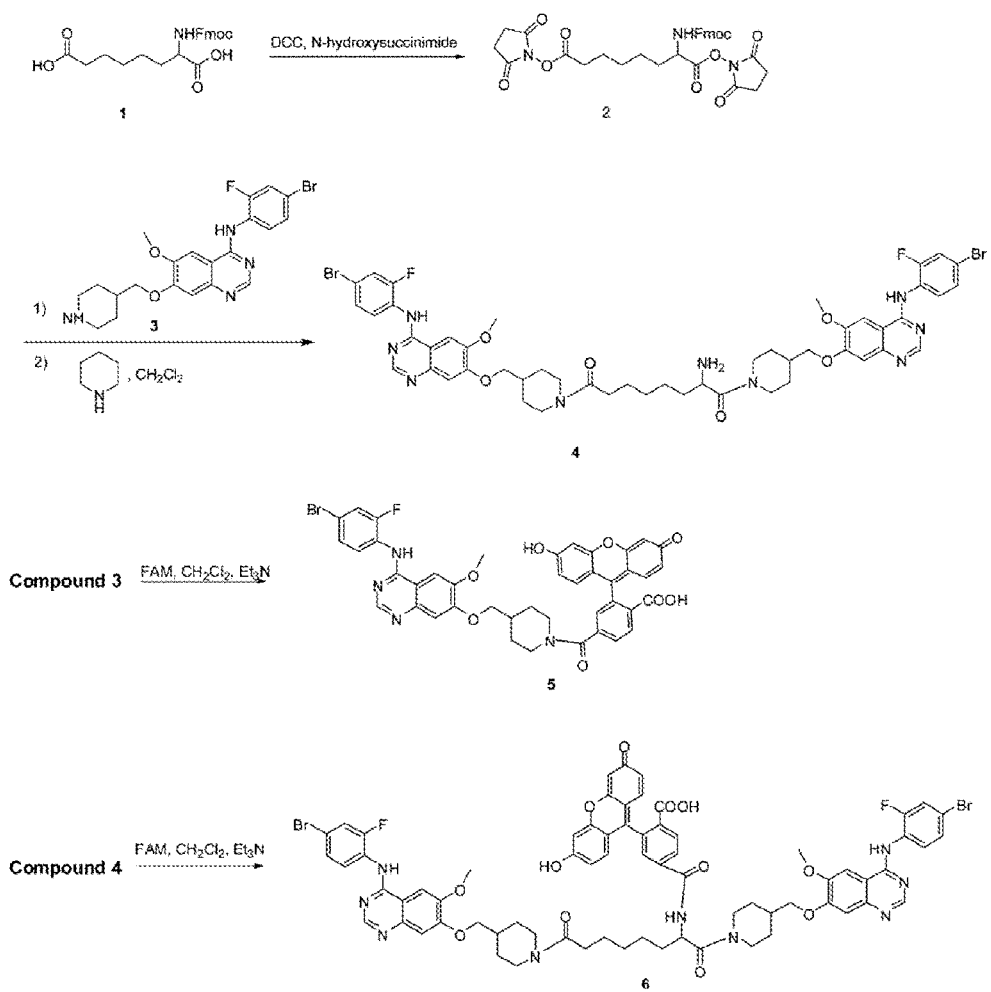
FIG. 8 shows the chemical structure of ZD 6474 monomer and a synthetic scheme for ZD6474 dimer, 6-FAM labeled ZD6474 monomer (5) and dimer (6).

ZD6474 (Vandetanib) Dimer Synthesis, FAM-Conjugated Monomer-ZD6474, and Dimer-ZD6474 Conjugate Synthesis Dimeric ligand ZD6474 was synthesized in three steps (FIG. 8). To the solution of compound 1, 2-(((9H-fluoren-9-yl)methoxy) carbonylamino)octanedioic acid (110 mg, 0.26 mmol) in EtOAc (20 mL), DCC (110 mg, 0.53 mmol), and N-hydroxysuccinimide (62 mg, 0.53 mmol) were added at 0° C. The mixture was stirred at 0° C. for 8 h (detected by TLC). The reaction mixture was filtrated to remove white solid and the solvent was evaporated under reduced pressure to get the crude intermediate 2. Compound 2 was dissolved in DCM (20 mL) for next step reaction without further purification. ZD6474, compound 3 (270 mg, 0.53 mmol), and DIPEA (0.2 mL) was added to the previous DCM solution of compound 2. The reaction mixture was stirred at ambient temperature for 24 h and the solvent was evaporated under reduced pressure. Ten mL 10% piperidine DCM solution was added and the mixture was stirred at room temperature for 2 h. The purification of the crude product was carried out on a semipreparative reversed-phase high-performance liquid chromatography (HPLC) system (Agilent 1200 series). Purification was performed on a Phenomenex Luna C18 (2) column 100R (250*10.00 mm). The flow was 4 mL/minute, with the mobile phase starting from 70% solvent A (0.05% TFA in water) and 30% solvent B (acetonenitile) to 50% solvent A and 50% solvent B at 20 min. Compound 4 was collected, lyophilized, and stored in the dark at −20° C. until use. 1H NMR (600 MHz, DMSO): 11.0 (s, active H), 8.74 (m, 2H), 8.14 (d, 2H), 8.02 (m, 2H), 7.77 (m, 2H), 7.56 (m, 4H), 7.38 (t, 2H), 4.04 (m, 10H), 3.60 (m, 1H), 3.21 (4H), 3.15 (m, 2H), 2.75 (m, 2H), 2.35 (m, 2H), 1.84 (m, 4H), 1.65 (m, 2H), 1.43 (m, 2H), 1.18 (m, 10H). MS (electrospray): m/z 1076.6 (100, [M+H]+, calcd 1075.8).

To a mixture of compound 3 (25 mg, 50 μmol), 6-carboxyfluorescein succinimidyl ester (FAM, 28 mg, 60 μmol) in 3 mL DCM, 100 μL triethyl amine was slowly added. After stirring overnight in the dark at ambient temperature, the reaction was quenched by adding 200 μL of TFA. The purification of the crude product 5 was carried out on a HPLC system (Agilent 1200 series). Purification was performed on a Phenomenex Luna C18(2) column 100R (250*10 mm). The flow was 4 mL/minute, with the mobile phase starting from 70% solvent A (0.05 M ammonia acetate in water) and 30% solvent B (acetonenitile) to 40% solvent A and 60% solvent B at 20 min. Compound 5 was collected, lyophilized, and stored in the dark at −20° C. until use. MS (electrospray): m/z 819.2 (100, [M+H]+, calcd 818.1). Compound 6 was prepared in the similar procedure described above and purified by HPLC. Compound 6 MS (electrospray): m/z 1434.1 (100, [M+H]+, calcd 1433.3). The absorption and fluorescence emission characteristics of compound 5 and 6 were identical to those of free FAM, as apparent from spectra measured in $H_2O$.

In Vitro Cellular Uptake

VEGFR-2 expression was established in three cell lines, MDA-MB-231 (human breast cancer cell line), U-87-MG (human glioblastoma brain cancer cell line), and HUVEC (human umbilical vascular endothelial cells). The cell lysate was separated by SDS-PAGE and transferred to nitrocellulose membranes. Membranes were probed with rabbit polyclonal antiphospho-VEGFR2 antibody (Cell Signaling Technology, Beverly, Mass.) followed by a goat antirabbit IgG horseradish peroxidase-conjugated secondary antibody; immunoreactive proteins were detected and visualized by chemiluminescence (ECL kit; Pierce, Rockford, Ill.). Proteins were separated by SDS-PAGE, and the phosphorylated proteins were probed with VEGFR-2 and antiphospho-VEGFR2. β-actin was used as a loading control.

Each of the FAM-conjugated compounds was incubated with MDA-MB-231 cells seeded 24 h earlier in a 96 well plate with 1% serum medium. Serial dilutions of the compounds were incubated for 3 h. The treated medium was then exchanged for fresh serum free medium. The remaining compound was then quantified from images taken using a Xenogen IVIS-200 (PerkinElmer, Inc. San Jose, Calif.) fluorescent imaging system. The same was done with HUVEC.

Blocking Assay

Specific binding of ZD6474-monomer and dimer were tested with blocking studies. Unlabeled ZD6474-monomer and ZD6474-dimer were mixed with the corresponding FAM-conjugated compounds simultaneously for 3 h. Plates were then imaged using the Xenogen IVIS-200 system. Similarly treated cells were fixed in 4% paraformaldehyde and imaged under fluorescent microscopy after staining the nuclei with DAPI.

Assay of In Vitro Cell Viability

MDA-MB-231 and U-87-MG cell lines were cultured in DMEM medium (Gibco, Grand Island, N.Y.) containing 10% fetal bovine serum (FBS) and 1% penicillin streptomycin at 37° C. in a humidified atmosphere of 5% $CO_2$ in air. HCT 116 (human, colorectal carcinoma cell line) was grown in McCoy's 5a medium modified with 10% FBS. HUVECs (Human Umbilical Vein Endothelial cells) were grown in EGM medium (Lonza), supplemented with 20% FBS, 100 U/mL penicillin, 100 µg/mL streptomycin at 37° C. under a humidified atmosphere of 5% $CO_2$ and 95% $O_2$ with same condition as above. For the cell viability assay, the cells were then seeded into 96-well flat-bottomed tissue-culture plates at 1×104 cells/well and incubated for 24 or 72 h in humidified atmosphere of 5% (v/v) $CO_2$ at 37° C. in the presence of each compound. For HUVECs, the flat-bottomed 96-well plate (Corning, N.Y., USA) was coated 1 h at 37° C. with gelatin (0.3% in PBS, pH 7.4) and then washed with PBS. The cells were then treated with ZD6474 monomer and its dimer compounds in the range from 5 nM to 100 µM concentration mixed with 1% FBS added culture medium (HUVECs was 2% FBS added). Following 24 and 72 h of incubation under 5% $CO_2$ at 37° C., the cells were washed with PBS and cell viability was assessed by MTT colorimetric assay. The absorbance of individual wells was measured by using an automated microplate reader (570 nm; VERSAmax, Molecular Devices Corp., Sunnyvale, Calif.). The data are expressed as the percentage of viable cells compared to the survival of a control group and were presented as mean±s.e. (n=6).

In Vitro Tubular Formation and In Vivo Angiogenesis Assessment Using the Matrigel Plug Assay Growth factor reduced Matrigel (100 µL, BD Bioscience, San Jose, Calif., USA) was added to each well of a 96-well plate and allowed to polymerize for 30 min at 37° C. HUVECs were suspended in the medium at the density of 4×10$^5$ cells per milliliter, and 0.1 mL of the cell suspension was added to each well coated with Matrigel in the presence of ZD6474 monomer or ZD6474 dimer Cells were incubated at 37° C. for 6 h, and then photographed. The branch points were counted and averaged.

The matrigel plug assays were performed injecting 637 µL of growth factor reduced liquid Matrigel-PBS mixture was into subcutaneously into the flanks of nu/nu nude mice at 4° C. Once inside the animals, the liquid Matrigel-PBS mixture solidifies. For comparison, Matrigel alone as well as Matrigel containing VEGF165 (Peprotech, Rocky Hill, N.J.) at a final concentration of 500 ng/mL to stimulate angiogenesis, and Matrigel with VEGF165 along with either ZD6474 monomer, ZD6474 dimer at a final concentration of 100 µM were used. All of the injection groups consisted of three mice. After 10 days, the mice were sacrificed and the Matrigel plugs were removed, fixed in 4% formalin and photographed.

In Vivo Animal Model and Ex Vivo Tumor Accumulation and Biodistribution Imaging Study The subcutaneous dorsa of five nu/nu female mice (6 weeks old; 20 g) were inoculated bilaterally with 1×10$^7$ U87-MG human glioblastoma cells overexpressing the VEGF receptor. Once the tumor diameter was approximately 7-8 mm at 21 days post implant, the mice were divided into three groups for the following injections: (a) free FAM (n=1), (b) FAM-labeled ZD6474-monomer (50 µM; n=2), and (c) FAM-labeled ZD6474-dimer (50 µM, n=2). The animals were manually restrained during intravenous tail injection. All tail vein injections were carried out with a 31 gauge needle placed in a lateral tail vein to inject 100 µL of solution. Twenty-four hours post injection, fluorescence images were acquired using a one second exposure time. The tumors and major organs were dissected and imaged again. Control (free FAM) and targeted (FAM labeled monomer and dimer) ex vivo tumor and organ tissue were imaged in parallel under fixed settings. In vivo fluorescence imaging was performed using the Xenogen IVIS 200 imaging system. To better observe the signal without losses and background due to intervening tissue, fluorescence images were collected ex vivo. Raw counts for each organ were measured using the Xenogen software by drawing oval regions of interest (ROI) around the organ of interest. The results were given as received photon flux per unit time in each of these ROIs, normalized by the incident light intensity. An estimate of the percentage of injected dose accumulated in the tumors was established by comparing measured counts/volume of tissue with the measured counts/volume of a known concentration of the same compound in water at the same exposure. A dilution low enough to avoid quenching was used and the results were linearly extrapolated to produce a conservative estimate of the compound concentration in the tissue. From there, the total amount of compound can be estimated and compared to the injected dose.

Statistics

The statistical significance of differences between interesting pairs of observations were determined using a twotailed Student's t test. A two parameter linear model was applied to the tubular networks data considering interaction of compound and dose. Statistical significance was considered to be present at P values <0.05.

Results

Figures 9A, 9B, 9C, 9D, 9E:
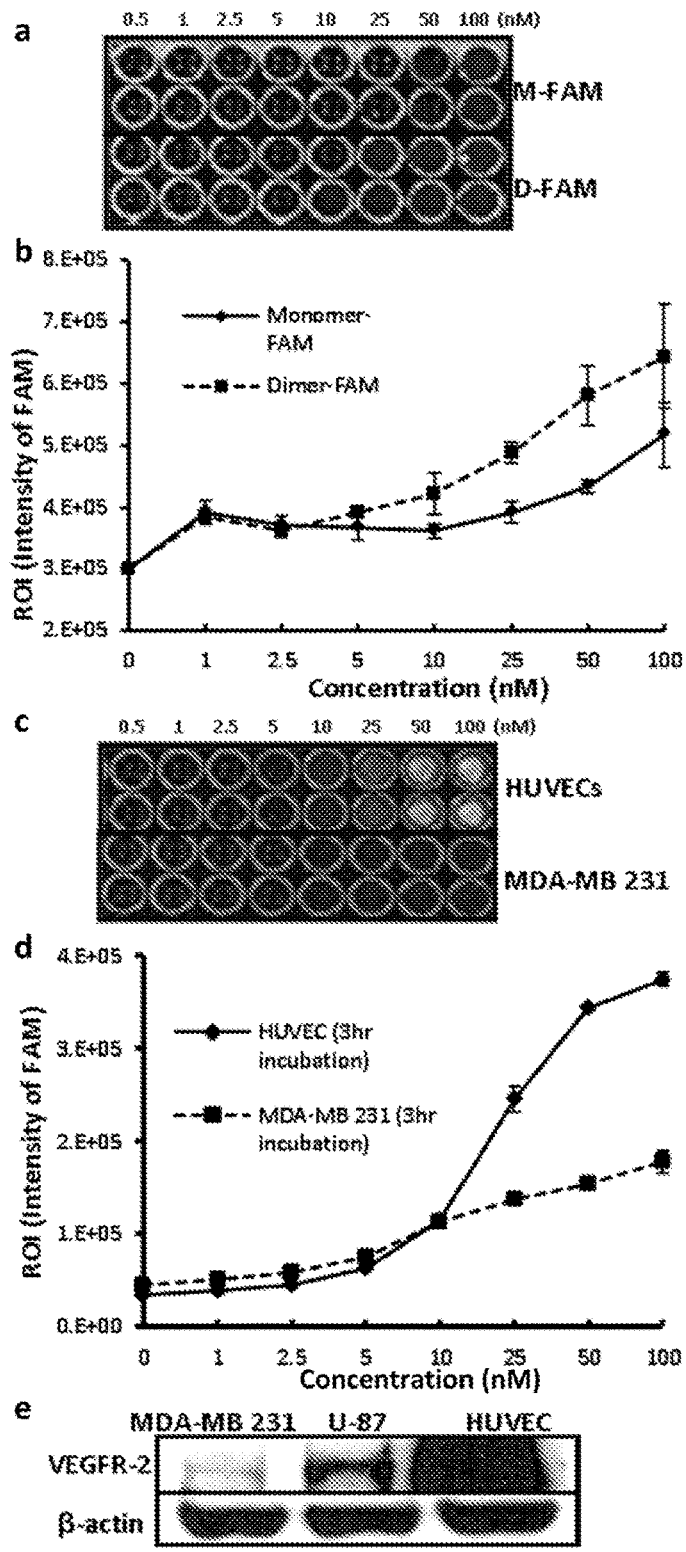
FIGS. 9A-9E are photographs and graphs showing the inhibition by ZD 6474-monomer, and ZD 6474-dimer

Cellular Uptake of FAM-Labeled ZD6474 Monomer and Dimer on MDA-MB-231 and HUVECS Based on in vitro assays, there appears to be minimal difference in uptake between monomer and dimer in the two cell lines, MDA-MB-231 and HUVECs (maximum P=0.09 for 100 nM dose; FIGS. 9A-9B). There was overall higher uptake of dimer-FAM by HUVECs rather than MDA-MB-231 cells (P<10-11 at 100 nM dose, FIGS. 9C-9D), although from 1 µM to 10 Mm concentration, the signal was almost the same for both cell lines (FIG. 9C). FIG. 9E shows comparative expression of VEGFR-2 in the three cell lines used in the studies, U-87 glioblastoma, MDA-MB-231, and HUVECs. U-87 shows higher expression compared to the MDA-MB-231 breast cancer cell line, with even more expression in the HUVEC cell line.

In Vitro Blocking of VEGF Receptor on HUVECs Using 6-FAM Labeled ZD6474-Dimer

Figures 10A, 10B, 10C:
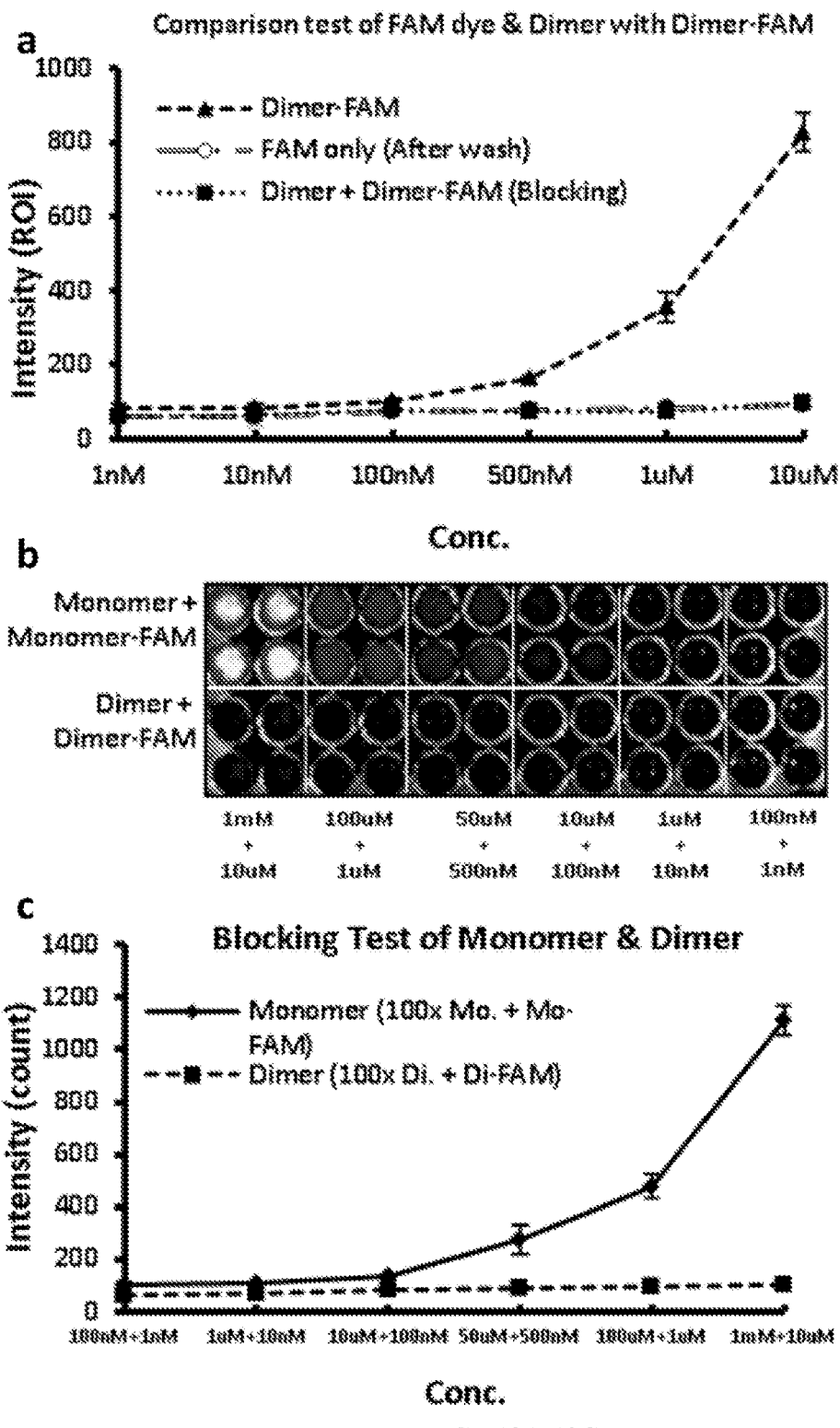
FIGS. 10A-10C show blocking test on HUVEC.
Figure 11:
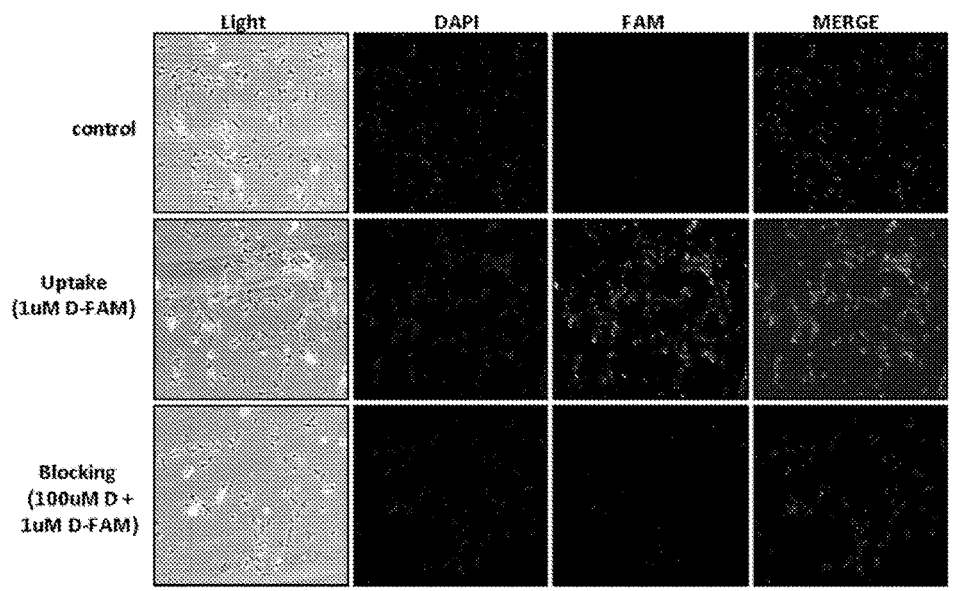
FIG. 11 shows cellular uptake images of HUVEC cells incubated with 1 μM FAM-conjugated ZD6474-dimer (uptake), 1 μL FAM-conjugated ZD6474-dimer and 100 μM ZD6474-dimer (blocking) and PBS (control). Complete blocking of fluorescence in blocking study demonstrated the high VEGFr specificity of the agent.

Results of the receptor blocking studies are shown in FIG. 10. A decrease in signal intensity due to receptor saturation by addition of excess (100× dose) of unlabeled compound, both monomer and dimer, is shown in FIG. 10B and quantified in FIGS. 10A and 10C. FIG. 10A shows almost 90% loss of dimer-FAM signal when mixed with unlabeled dimer (P<10-6 for 10 µM dose). This is nearly identical to the signal from nonspecific binding of FAM. FIG. 10C directly compares the blocking of monomer and dimer, with the dimer showing much stronger blocking and specificity. The mean signal from blocked monomer-FAM is over 10× greater than the same from dimer FAM (P<10-7 for 10 µM dose). The intracellular distribution of the FAM-labeled dimer is shown in FIG. 11, with and without blocking via cold dimer.

In Vitro Cytotoxicity of Monomer and Dimer

Figures 12A, 12B, 12C, 12D:
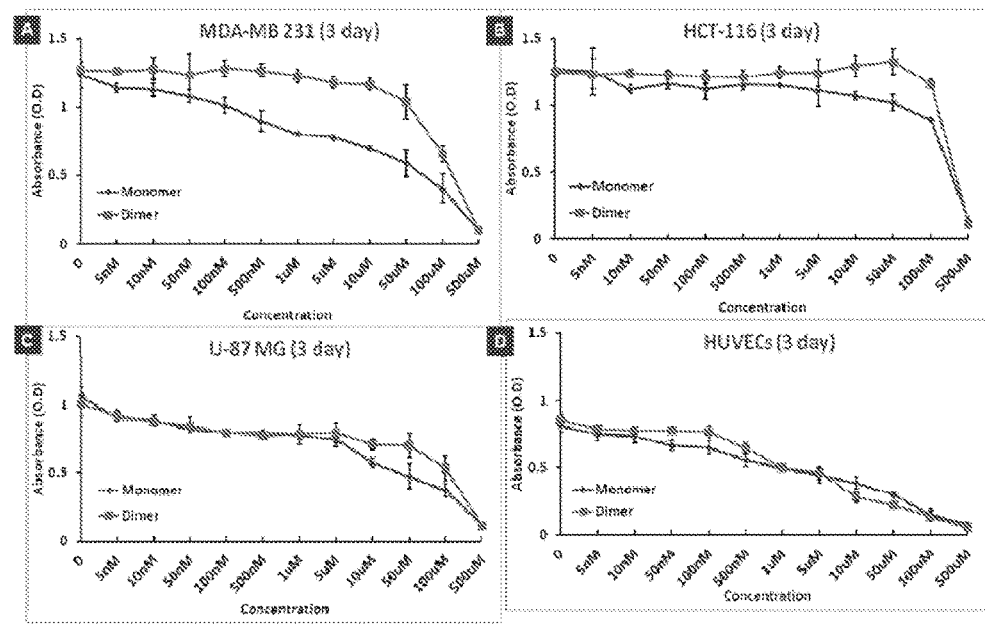
FIGS. 12A-12D are graphs showing in vitro cytotoxicity of ZD 6474-monomer and ZD 6474-dimer against several types of cell line. The graphs represent cytotoxicity in MDA-MB 231 (FIG. 12A), HCT-116 (FIG. 12B), U-87 MG (FIG. 12C), and HUVEC (FIG. 12D) cell lines after the incubation of 72 h. The results represent the means±SDs (n=6).

The cytotoxicity of ZD6474-monomer and ZD6474-dimer on cultured MDA-MB-231 (human breast cancer), HCT-116 (human colon cancer), U-87-MG (human brain glioblastoma), and HUVECS (human endothelial cells) are shown in FIG. 12. Both drugs showed low toxicity to the cancer cells for a wide range of concentrations in the experimental range from 5 nM to 50 µM. Even at 100 µM, around 50% of cells treated with the monomer or dimer remained viable for the cancer cell lines (FIGS. 12A-12C). In HUVECs, however, both monomer and dimer began to affect cell viability starting at the 500 nM concentration. From this dose and upward, endothelial cells are dying (FIG. 12D).

Inhibitory Effect of ZD6474 Derivatives on Angiogenesis In Vitro and In Vivo

Figures 13A, 13B, 13C:
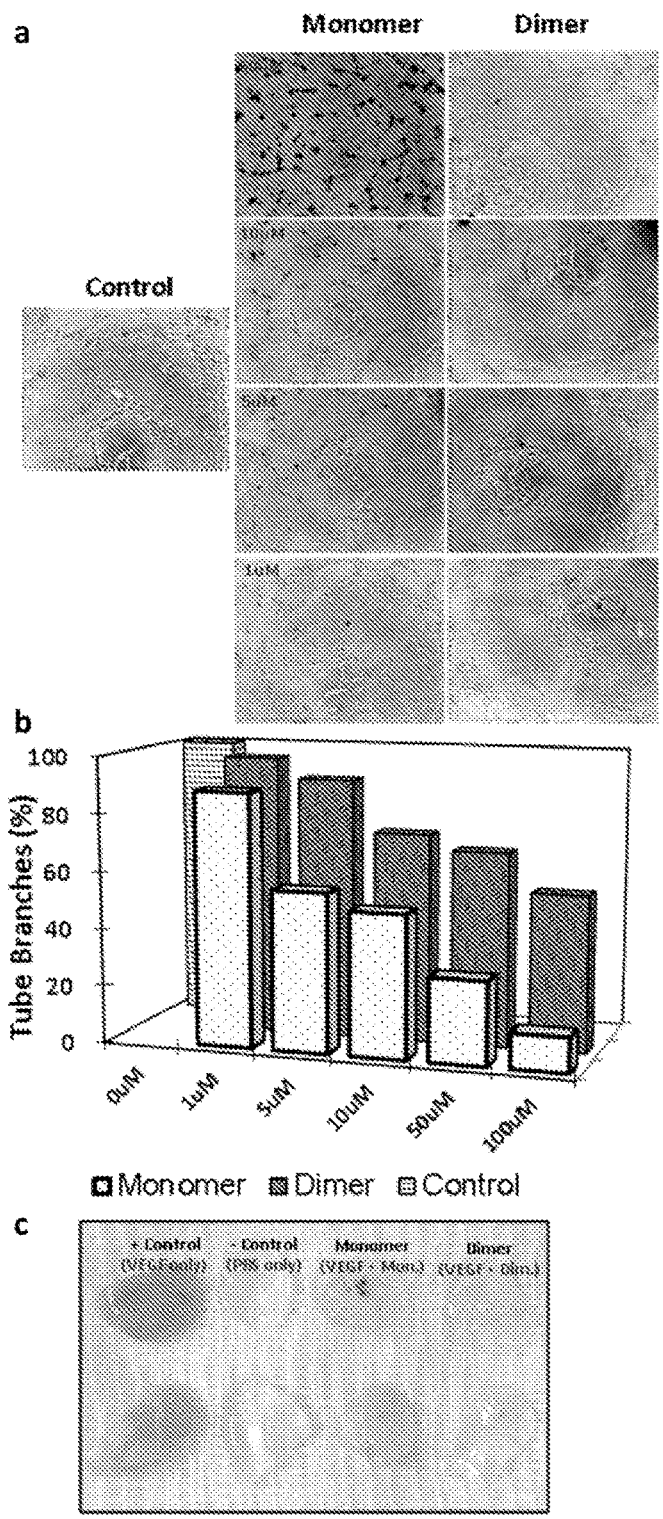
FIG. 13A contain photographs showing in vitro tubular formation in HUVEC cells.
FIG. 13B is a graph quantifying the branches in FIG. 13A.
FIG. 13C is a photograph representing results from an in vivo matrigel plug assay. The matrigel contained VEGF165 (final concentration of 500 ng/mL) and ZD 6474 monomer or ZD 6474 dimer (final concentration of 100 μM). The matrigel were inserted into mice for 10 days. The mice were then sacrificed and the matrigel plugs removed, fixed in 4% PFA (para-formaldehyde), then photographed.

Cell alignments and tubular structure formations were observed in control wells of HUVECs. Cells treated with ZD6474 derivatives showed inhibitory effects (FIG. 13A). ZD6474-monomer exhibited greater inhibitory effect against cell alignment and tubular structure formation than ZD6474-dimer (P=0.005). Both monomer and dimer demonstrated a strong dose-dependent inhibition of tube formation (P<10-4), with the dose effect somewhat stronger in the monomer (P=0.05). The number of tube branches was reduced from 100% in the control group to 52.0±4.8% (ZD6474-monomer, 10 µM) and 75±5.2% (ZD6474-dimer, 10 µM), respectively (FIG. 13B). As the incubation period continued to 6 h, HUVECs treated with both ZD6474 derivatives gradually lost intercellular contact.

Figures 14A, 14B, 14C, 14D:
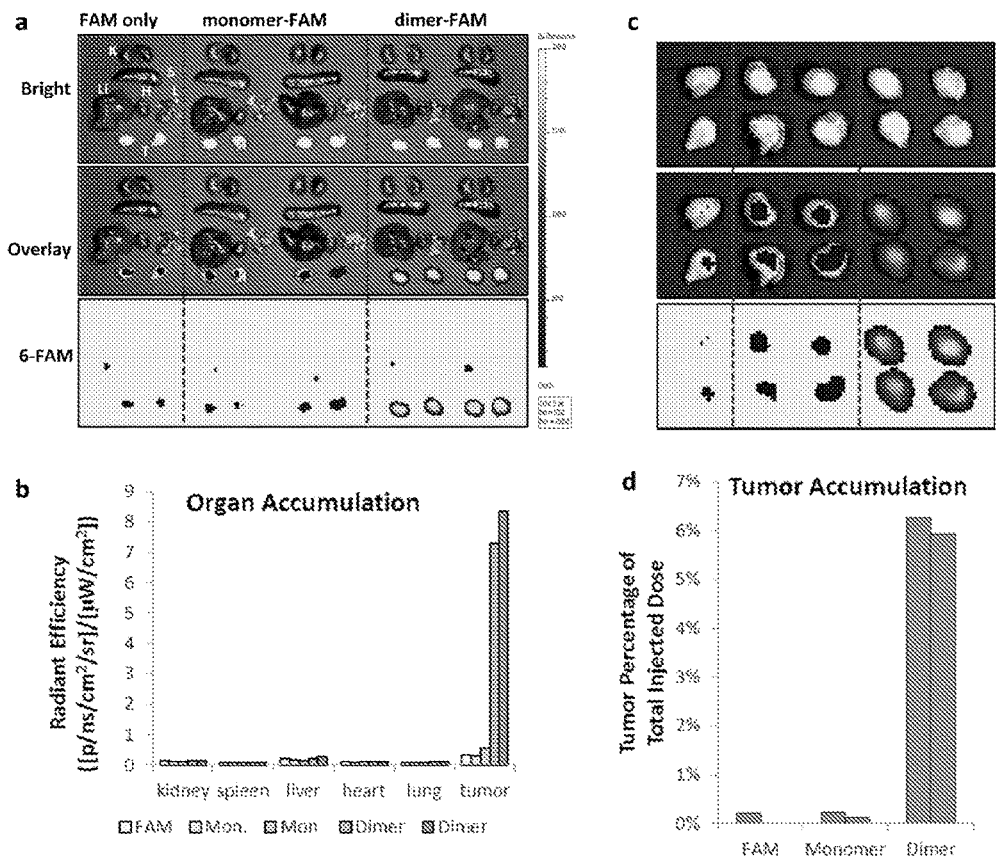
FIGS. 14A-14D show ex vivo images of tissue distribution of FAM dye, and FAM-dye conjugated ZD6474 monomer and dimer in a bilateral U-87 tumor xenograft model in 5 animals. Images are taken and analyzed 24 h after i.v. injection of compound using a Xenogen IVIS 200 imaging box in a single exposure.

FIG. 13C showed the in vivo effect on of the compounds on angiogenesis determined by the matrigel plug assay. The plugs treated with VEGF165 alone were dark red in color, indicating the formation of new blood vessels and existing red blood cells in circulation. Negative controls showed no such color. Plugs mixed with ZD6474-monomer were paler in color than the positive controls but not entirely clear, implying significant inhibition of blood vessel development within the matrigel. On the other hand, plugs treated with ZD6474-dimer and VEGF165 were almost the same as the PBS treated negative control group. These results show that ZD6474-dimer was more effective in preventing microvessel formation of VEGF165-induced angiogenesis than ZD6474-monomer in vivo. Ex Vivo Imaging of VEGF Overexpression in Xenograft U-87 Tumor After the i.v. injection of 6-FAM-labeled ZD6474 derivatives in mice carrying subcutaneous xenografts of U-87 glioblastoma, the fluorescence intensity immediately increased in the whole body, due to the rapid circulation of 6-FAMlabeled ZD6474 derivatives. However, the NIR fluorescence signal in the whole body decreased as the time elapsed. The 6-FAM-labeled ZD6474-dimer displayed stronger fluorescence signals than ZD6474-monomer in the tumor regions compared to whole body. Ex vivo images at the 24 h time point following i.v. injection showed about 20× greater fluorescent intensity coming from the ZD6474-dimer group tumors than from tumors in other groups and from organs (FIG. 14A-A4B). Tumor uptake of FAM dye, monomer-FAM, and dimer-FAM (FIG. 14C), when compared with images of known dye concentrations, demonstrated that at least 6% of the total injected dose of the dimer-FAM ended up in the tumors compared to less than 0.25% of both FAM and monomer-FAM (FIG. 14D). Despite the low sample numbers, the difference is highly significant, with P<0.001 using a two-sided t test.

VEGFR Cell Receptor-Binding Assay

Figure 15:
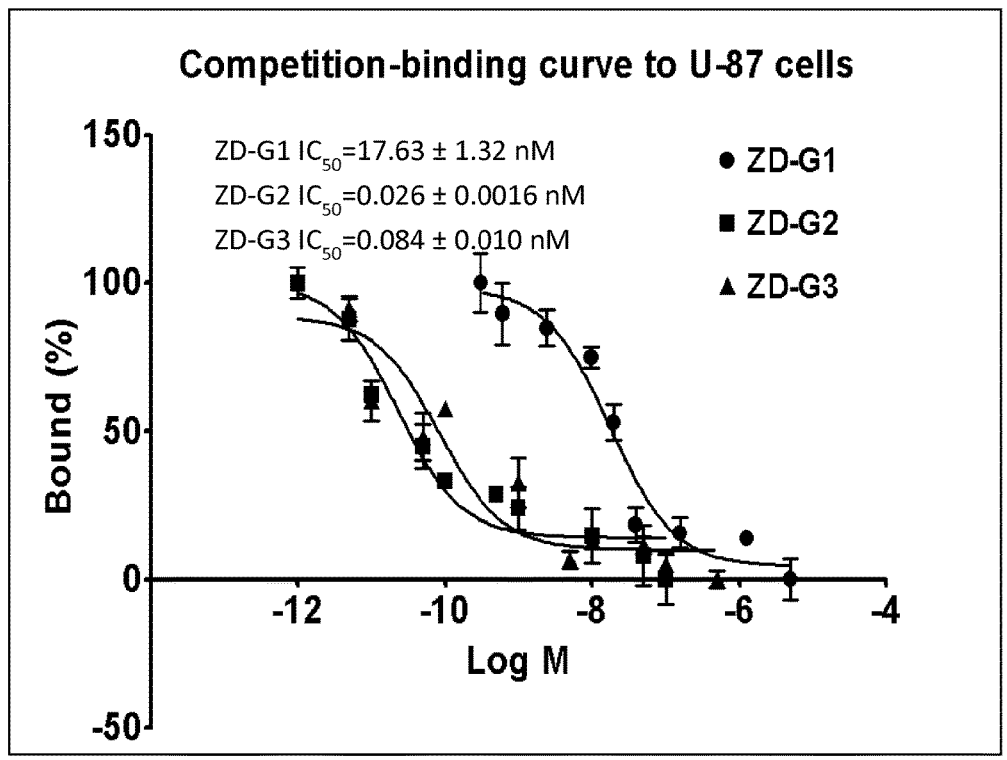
FIG. 15 is competition-binding curve of ZD-G1, ZD-G2 and ZD-G3 to U-87 cells. Log of concentration of competitor compounds versus percentage of maximum specific binding of radiolabeled molecules.

VEGFR binding affinity and specificity of the ZD-G1, ZD-G2 and ZD-G3 were evaluated by competition assays using U-87 MG cells. Cells were seeded in 12-well plates at a density about 5×105 cells per well the day before the experiment. For the displacement/competition assay, non-radioactive ZD-G1, ZD-G2 and ZD-G3 were dissolved in FBS-free DMEM medium, and serially diluted in gradient concentration. The HPLC purified radio-tracer was re-dissolved in FBS-free DMEM medium and diluted to 1 uCi/100 uL. The U-87 MG cells were incubated with 1 uCi 64Cu-DOTA-ZD-G2 per well and co-incubation with serial concentration of non-radioactive ZD-G1, ZD-G2 and ZD-G3 respectively. After incubation at 4° C. for 1 hour, the supernatant with free radio tracer was removed carefully and the cells were then washed with cold PBS for three times and trypsinized. The cells were collected and cell pellet associated radioactivity was measured and the binding affinity values ($IC_{50}$) were calculated by nonlinear regression using GraphPad Prism (GraphPad Software, CA). All experiments were carried out in triplicate. The binding assay of the ZD-G1, ZD-G2 and ZD-G3 to U-87 MG cells yielded a $IC_{50}$ value of 17.6, 0.026 and 0.084 nM, respectively. The results are shown in FIG. 15.

Figure 16:
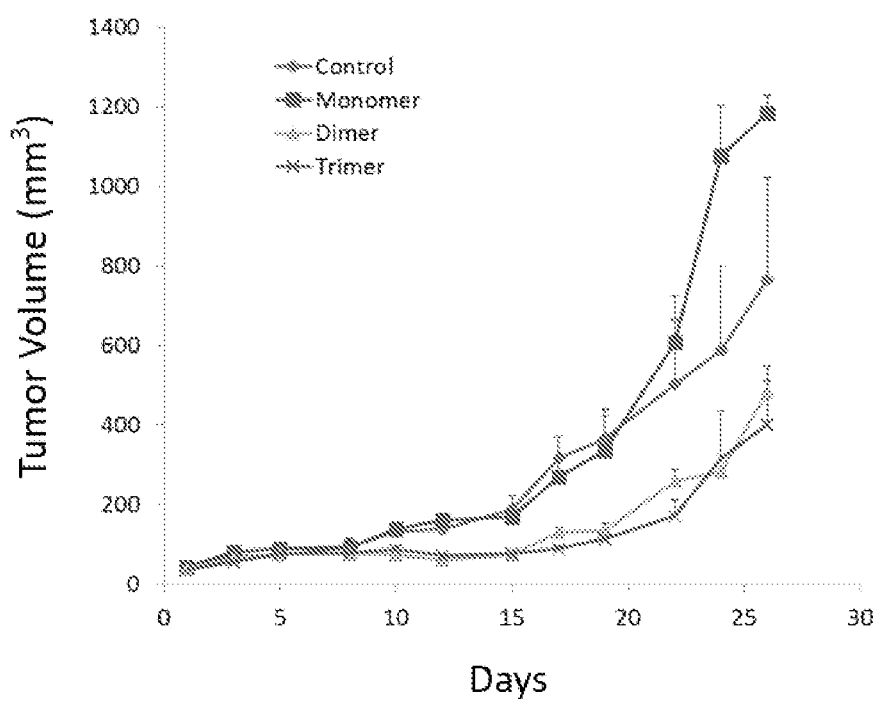
FIG. 16 is a graph showing the in vivo antitumor activity of vehicle, monomer ZD-G1, dimer ZD-G2, and trimer ZD-G3 after administration i.v. three times per week of similar pharmacological dose. The results show the means±SD (n=5) (P<0.05).

In Vivo Antitumor Efficacy of Multivalent IAs (FIG. 16)

All animal procedures were approved by the Methodist Hospital Research Institute Animal Care and Use Committee. The therapeutic test for antitumor efficacy of ZD compounds was evaluated using tumor-bearing mice which were prepared by subcutaneous injection in the thighs of nu/nu female mice (6 weeks old; 20-25 g). The mouse glioblastoma cancer cell line U87 was obtained from Caliper and tested negative for rodent pathogens. The mice were inoculated with suspensions of 1×10$^6$ U87 cells in 100 µl complete medium (10% FBS added). About 10 days after subcutaneous inoculation (the tumor diameter was approximately 3-5 mm, the tumor volume was approximately 50 to 100 mm$^3$), tumor-bearing mice (n=6 per group) were injected intravenously (i.v.) with each ZD compounds (monomer ZD-G1, dimer ZD-G2, trimer ZD-G3) at 20 mg/kg per injection three times per week resulting in equivalent pharmacophore. The tumor size was calculated as a×b$^2$/2, where 'a' is the largest and 'b' the smallest diameter.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound of Formula II:

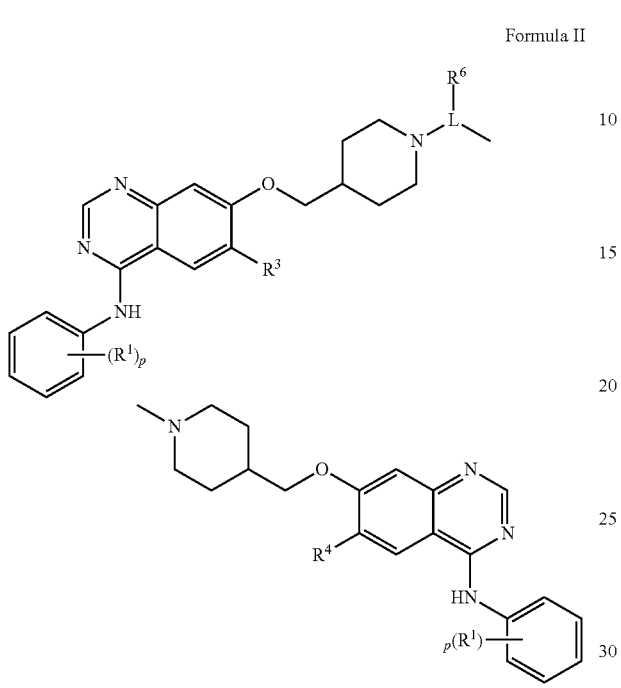

Formula II wherein,

R$^1$ is hydroxyl, halogen, C$_{1-3}$ alkyl, C$_{1-3}$ alkoxyl, C$_{1-3}$ alkanoyloxy, trifluoromethyl, cyano, amino, or nitro;

R$^3$ and R$^4$ are, independently of one another, hydrogen, hydroxyl, halogen, nitro, trifluoromethyl, cyano, C$_{1-3}$ alkyl, C$_{1-3}$ alkoxyl, C$_{1-3}$ alkylthio, or —NR$^7$R$^8$, wherein R$^7$ and R$^8$, which can be the same or different, each represents hydrogen or C$_{1-3}$ alkyl;

R$^6$ is a detectable moiety chosen from a chelated radionuclide, Pd (II) octaethylporphyrin, Pt (II)-octaethylporphyrin, Pd (II) tetraphenylporphyrin, Pt (II) tetraphenylporphyrin, Pd (II) meso-tetraphenylporphyrin tetrabenzoporphine, Pt (II) meso-tetrapheny metrylbenzoporphyrin, Pd (II) octaethylporphyrin ketone, Pt (II) octaethylporphyrin ketone, Pd (II) meso-tetra(pentafluorophenyl)porphyrin, Pt (II) meso-tetra (pentafluorophenyl) porphyrin, Ru (II) tris(4, 7-diphenyl-1,10-phenanthroline) (Ru (dpp)$_3$), Ru (II) tris(1,10-phenanthroline) (Ru(phen)$_3$), tris(2,2'-bipyridine) ruthenium (II) chloride hexahydrate (Ru(bpy)$_3$), erythrosine B, fluorescein, eosin, iridium (III) ((N-methyl-benzimidazol-2-yl)-7-(diethylamino)-coumarin)), indium (III) ((benzothiazol-2-yl)-7-(diethyl amino)-coumarin))-2-(acetylacetonate), Macroflex fluorescent red, Macrolex fluorescent yellow, Texas Red, rhodamine B, rhodamine 6G, sulfur rhodamine, m-cresol, thymol blue, xylenol blue, cresol red, chlorophenol blue, bromocresol green, bromcresol red, bromothymol blue, a Cy2 moiety, a Cy3 moiety, a Cy5 moiety, a Cy5.5 moiety, a Cy7 moiety, 4-nitrophenol, alizarin, phenolphthalein, o-cresolphthalein, chlorophenol red, calmagite, bromo-xylenol, phenol red, neutral red, nitrazine, 3,4,5,6-tetrabromphenolphtalein, congo red, 2',7'-dichlorofluorescein, 5(6)-carboxy-fluorescein, carboxynaphtofluorescein, 8-hydroxypyrene-1,3,6-trisulfonic acid, semi-naphthorhodafluor, semi-naphthofluorescein, tris (4,7-diphenyl-1,10-phenanthroline) ruthenium (II) dichloride, (4,7-diphenyl-1,10-phenanthroline) ruthenium (II) tetraphenylboron, platinum (II) octaethylporphyin, dialkylcarbocyanine, and dioctadecylcycloxacarbocyanine, or R$^6$ is a therapeutic moiety chosen from doxorubicin, doxorubicin substituted with fluorescein, or vandetanib;

p is an integer from 1 to 4; and

L is —(CO—R$^{14}$)$_3$N, —(R$^{14}$)$_3$N, —(SO$_2$R$^{14}$)$_3$N, —(SOR$^{14}$)$_3$N, —(OR$^{14}$)$_3$N, —(O—CO—R$^{14}$)$_3$N, —(CO—O—R$^{14}$)$_3$N, —(CO—R$^{14}$)$_3$CH, —(R$^{14}$)$_3$CH, —(SO$_2$R$^{14}$)$_3$CH, —(SOR$^{14}$)$_3$CH, —(O—CO—R$^{14}$)$_3$CH, or —(OR$^{14}$)$_3$CH wherein R$^{14}$ is C$_1$-C$_{20}$ alkyl; C$_1$-C$_{20}$ heteroalkyl; C$_1$-C$_{20}$ alkylamine; C$_1$-C$_{20}$ alkoxy; C$_1$-C$_{20}$ alkanoyloxy; or C$_1$-C$_{20}$ alkylamido.

2. The compound of claim 1,

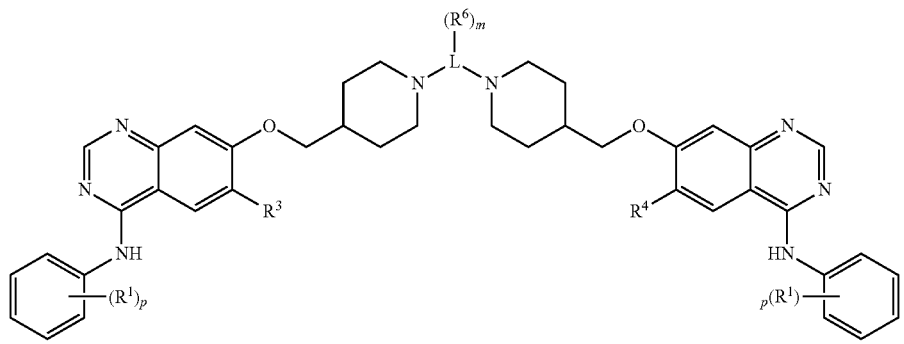

wherein,

R$^1$ is hydroxyl, halogen, C$_{1-3}$ alkyl, C$_{1-3}$ alkoxyl, C$_{1-3}$ alkanoyloxyl, or trifluoromethyl; and R$^3$ and R$^4$ are independently hydrogen, hydroxyl, halogen, C$_{1-3}$ alkyl, C$_{1-3}$ alkoxyl, or C$_{1-3}$ alkylthio.

3. The compound of claim 1, wherein the detectable moiety is fluorescein, rhodamine, Texas Red, a Cy2 moiety, a Cy3 moiety, a Cy5 moiety, a Cy5.5 moiety, or a Cy7 moiety.

4. The compound of claim 1, wherein the detectable moiety is the chelated radionuclide and the radionuclide is selected from the group consisting of $^{18}$F, $^{64}$Cu, $^{67}$Cu, $^{89}$Zr, $^{111}$In, $^{124}$I, $^{123}$I, and $^{99m}$Tc.

5. The compound of claim 1, wherein the linker is —(CO—O—R$^{14}$)$_3$N or —(CO—O—R$^{14}$)$_3$CH, wherein R$^{14}$ is a C$_{2-4}$ alkyl.

6. The compound of claim 1, having Formula III:

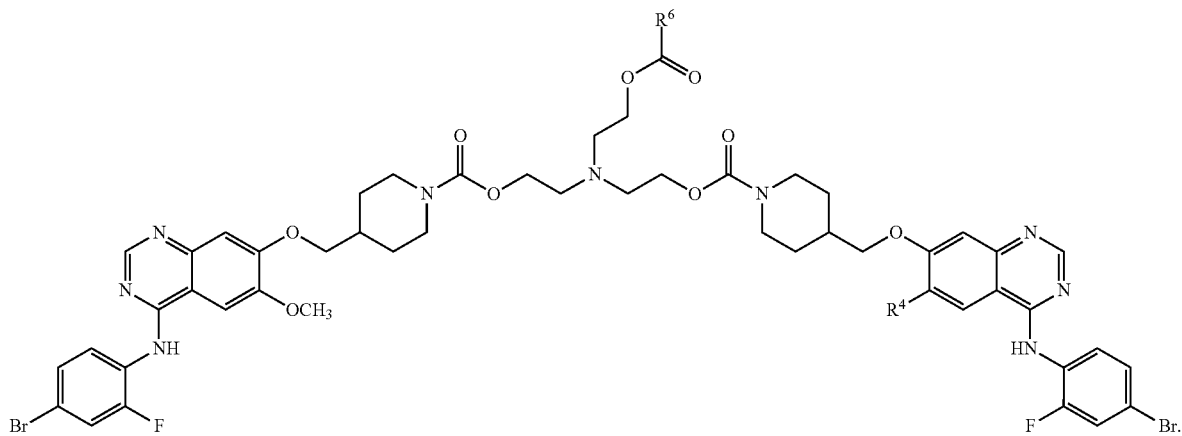

Formula III

7. The compound of claim 1, wherein $R^6$ is the chelated radionuclide and the chelator is 2,2',2''-(10-(2-((2,5-dioxopyrrolidin-1-yl)oxy)-2-oxoethyl)-1,4,7,10-tetraazacyclododecane-1,4,7-triyl)triacetic acid (DOTA) or diethylene triamine pentaacetic acid (DTPA).

8. The compound of claim 1, wherein $R^6$ is vandetanib.

9. The compound of claim 1, having Formula VII,

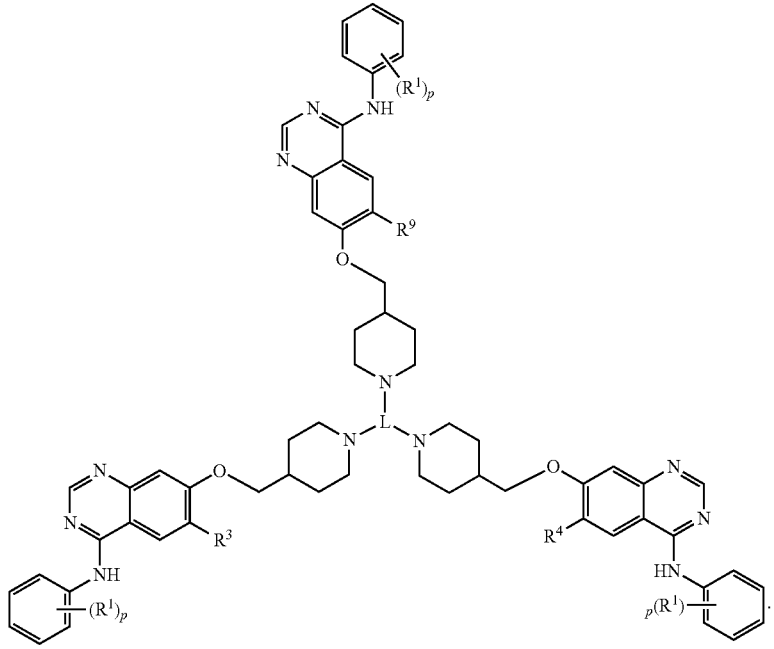

Formula VII

10. The compound of claim 9, wherein the linker is —(CO—O—$R^{14}$)$_2$NH or —(CO—O—$R^{14}$)$_2$CH$_2$, wherein $R^{14}$ is a $C_{1-4}$ alkyl.

11. The compound of claim 1, having the structure

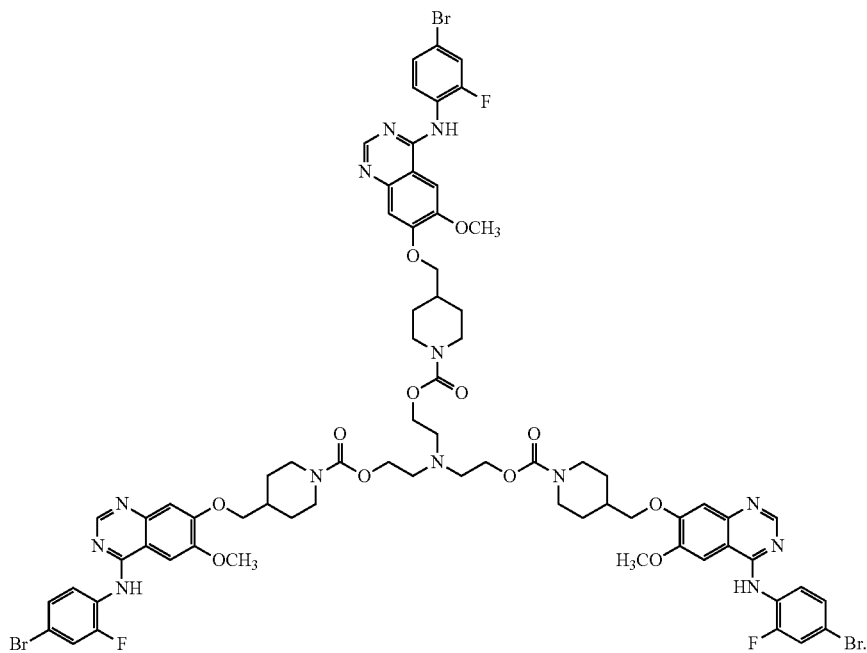 [SMILES: COc1cc2c(Nc3ccc(Br)cc3F)ncnc2cc1OCC1CCN(C(=O)OCCN(CCOC(=O)N2CCC(COc3cc4ncnc(Nc5ccc(Br)cc5F)c4cc3OC)CC2)CCOC(=O)N2CCC(COc3cc4ncnc(Nc5ccc(Br)cc5F)c4cc3OC)CC2)CC1]

12. A method for detecting or imaging cells expressing vascular endothelial growth factor receptor in a mammal, the method comprising administering to the mammal a compound of claim 1, in an amount and for a time sufficient to detect or image at least a population of the cells expressing vascular endothelial growth factor receptors in the mammal to which the detectable moiety is bound.

13. The method of claim 12, wherein the detectable moiety is identifiable by confocal microscopic imaging, CT imaging, PET imaging, MRI, or any combination thereof.

14. A method for imaging a population of cells expressing vascular endothelial growth factor receptor within or about the body of an animal, the method comprising administering to the animal an amount of a compound of claim 1, and for a time effective to image a population of cells expressing vascular endothelial growth factor receptor within or about the body of the animal.

15. The method of claim 14, wherein the population of cells expressing vascular endothelial growth factor receptor comprises cancer cells, tumor cells, hyperproliferative cells, or any combination thereof.

16. The method of claim 14, wherein the animal is a human diagnosed with cancer.

* * * * *